United States Patent
Baileykobayashi et al.

(10) Patent No.: US 10,981,953 B2
(45) Date of Patent: Apr. 20, 2021

(54) METHOD FOR PROMOTING EXPRESSION OF CALRETICULIN, AND SYNTHETIC PEPTIDE FOR USE IN METHOD FOR PROMOTING EXPRESSION OF CALRETICULIN

(71) Applicants: TOAGOSEI CO., LTD., Tokyo (JP); KYOTO UNIVERSITY, Kyoto (JP)

(72) Inventors: Nahoko Baileykobayashi, Tsukuba (JP); Tetsuhiko Yoshida, Tsukuba (JP); Yoshinori Yoshida, Kyoto (JP); Kazuhisa Chonabayashi, Kyoto (JP)

(73) Assignees: TOAGOSEI CO, LTD., Tokyo (JP); KYOTO UNIVERSITY, Kyoto (JP)

(*) Notice: Subject to any disclaimer, the term of this patent is extended or adjusted under 35 U.S.C. 154(b) by 107 days.

(21) Appl. No.: 15/108,349

(22) PCT Filed: Dec. 24, 2014

(86) PCT No.: PCT/JP2014/084145
§ 371 (c)(1),
(2) Date: Jun. 27, 2016

(87) PCT Pub. No.: WO2015/098963
PCT Pub. Date: Jul. 2, 2015

(65) Prior Publication Data
US 2016/0318975 A1  Nov. 3, 2016

(30) Foreign Application Priority Data
Dec. 26, 2013 (JP) ............... JP2013-270470

(51) Int. Cl.
| A61K 38/10 | (2006.01) |
| A61K 38/08 | (2019.01) |
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| C07K 7/08 | (2006.01) |
| C07K 7/06 | (2006.01) |
| C07K 14/47 | (2006.01) |
| C07K 14/705 | (2006.01) |
| A61K 38/00 | (2006.01) |

(52) U.S. Cl.
CPC ............... C07K 7/08 (2013.01); A61K 38/04 (2013.01); A61K 38/08 (2013.01); A61K 38/10 (2013.01); C07K 7/06 (2013.01); C07K 14/4725 (2013.01); C07K 14/705 (2013.01); A61K 38/00 (2013.01); C07K 2319/03 (2013.01); C07K 2319/10 (2013.01)

(58) Field of Classification Search
None
See application file for complete search history.

(56) References Cited

U.S. PATENT DOCUMENTS

| 4,945,102 A | 7/1990 | Suzuki et al. | |
| 7,597,890 B2* | 10/2009 | Chinnaiyan | C07K 14/4748 424/133.1 |
| 9,296,787 B2* | 3/2016 | Kobayashi | A61K 38/08 |
| 9,353,350 B2* | 5/2016 | Kobayashi | C07K 7/06 |
| 9,353,351 B2* | 5/2016 | Kobayashi | C07K 14/47 |
| 9,551,720 B2* | 1/2017 | Singbartl | G01N 33/6893 |
| 2004/0034888 A1* | 2/2004 | Liu | C07H 21/04 800/289 |
| 2006/0122122 A1* | 6/2006 | Kobayashi | A61K 38/08 514/2.4 |
| 2008/0248037 A1* | 10/2008 | Li | A61P 25/00 424/138.1 |
| 2009/0053807 A1* | 2/2009 | Pillutla | C07K 14/62 435/375 |
| 2010/0227339 A1* | 9/2010 | Yoon | G01N 33/56983 435/7.92 |
| 2010/0297758 A1 | 11/2010 | Yoshida et al. | |
| 2012/0035112 A1 | 2/2012 | Yoshida et al. | |
| 2012/0122210 A1* | 5/2012 | Yoshida | C07K 7/08 435/366 |
| 2013/0079273 A1 | 3/2013 | Yoshida et al. | |
| 2013/0143757 A1* | 6/2013 | Zhong | G01N 33/6893 506/9 |
| 2015/0004697 A1 | 1/2015 | Kobayashi et al. | |
| 2015/0018286 A1 | 1/2015 | Kobayashi et al. | |
| 2015/0273018 A1 | 10/2015 | Kobayashi et al. | |
| 2016/0346346 A1* | 12/2016 | Baileykobayashi | A61K 38/08 |

FOREIGN PATENT DOCUMENTS

| CN | 1393461 A * | 1/2003 | |
| JP | H08-19111 B2 | 2/1996 | |
| JP | 2668232 B2 | 10/1997 | |
| JP | 5328357 B2 | 10/2013 | |
| WO | 8802366 A1 | 4/1988 | |
| WO | 2007/048002 A2 | 4/2007 | |
| WO | WO-2007097923 A2 * | 8/2007 | ............ G16C 20/60 |
| WO | 2009093692 A1 | 7/2009 | |
| WO | WO-2010106437 A1 * | 9/2010 | ............ A23J 3/34 |
| WO | 2010/117079 A1 | 10/2010 | |

(Continued)

OTHER PUBLICATIONS

UniProt Accession No. A0A0A1GQ78, 3 pages (2015) (Year: 2015).*
UniProt Accession No. A0A0T7A9B4, 3 pages (2016) (Year: 2016).*
UniProt Accession No. I9WRI3, 3 pages (2012) (Year: 2012).*
UniProt Accession No. A0A0E9U1W7, 2 pages (2015) (Year: 2015).*
UniProt Accession No. P76345, 5 pages (1997) (Year: 1997).*

(Continued)

*Primary Examiner* — Thea D' Ambrosio
(74) *Attorney, Agent, or Firm* — Oliff PLC

(57) ABSTRACT

A method for promoting expression of calreticulin in at least one kind of eukaryotic cell, and a synthetic peptide useful in this method are provided. In the method provided by the present invention, a culture of target cells is prepared, and a calreticulin expression-promoting peptide having calreticulin expression-promoting activity is supplied at least once to that culture.

11 Claims, 9 Drawing Sheets

Specification includes a Sequence Listing.

(56) References Cited

FOREIGN PATENT DOCUMENTS

| WO | WO-2011078351 A1 * | 6/2011 | ............ C12P 21/02 |
|---|---|---|---|
| WO | 2011/152524 A1 | 12/2011 | |
| WO | WO-2012027282 A2 * | 3/2012 | ........... C12N 9/0004 |
| WO | WO 2012027282 A2 * | 3/2012 | ........... C12N 9/0004 |
| WO | WO-2013039857 A1 * | 3/2013 | ............ C07H 21/02 |
| WO | WO-2013041962 A1 * | 3/2013 | ......... A61K 39/0007 |
| WO | 2013/094697 A1 | 6/2013 | |
| WO | 2013/094698 A1 | 6/2013 | |
| WO | WO-2013143026 A1 * | 10/2013 | ............ C40B 40/10 |
| WO | 2014/061749 A1 | 4/2014 | |

OTHER PUBLICATIONS

UniProt Accession No. Q9PAW8, 3 pages (2000) (Year: 2000).*
UniProt Accession No. P10636, 33 pages (2011) (Year: 2011).*
UniProt Accession No. A0A1P8PKI7, 3 pages (2017) (Year: 2017).*
UniProt Accession No. A0A0E9T6M5, 3 pages (2015) (Year: 2015).*
UniProt Accession No. P50716, 6 pages (1997) (Year: 1997).*
UniProt Accession No. A0A0E9S6R0, 3 pages (2015) (Year: 2015).*
UniProt Accession No. P13476, 5 pages (1990) (Year: 1990).*
UniProt Accession No. A0A0N0WZH7, 3 pages (2015) (Year: 2015).*
UniProt Accession No. A0A1B6KB79, 4 pages (2016) (Year: 2016).*
UniProt Accession No. A0A1Q3N9V6, 3 pages (2017) (Year: 2017).*
UniProt Accession No. A0A1A8RY52, 2 pages (2016) (Year: 2016).*
UniProt Accession No. A0A0E9XEJ7, 2 pages (2015) (Year: 2015).*
UniProt Accession No. F7F2Y2, 4 pages (2011) (Year: 2011).*
UniProt Accession No. S9YB41, 6 pages (2013) (Year: 2013).*
UniProt Accession No. A2R2V9, 7 pages (2007) (Year: 2007).*
UniProt Accession No. H0VZS1, 6 pages (2017) (Year: 2017).*
UniProt Accession No. A0A0U0SBZ3, 3 pages (2016) (Year: 2016).*
UniProt Accession No. A0A1B8YAF1, 3 pages (2016) (Year: 2016).*
UniProt Accession No. A0A167H712, 3 pages (2016) (Year: 2016).*
Adessi et al., Curr. Med. Chem. 9:963-978 (2002) (Year: 2002).*
Apr. 7, 2015 Written Opinion of the International Searching Authority issued in International Patent Application No. PCT/JP2014/084145.
Apr. 7, 2015 Search Report issued in Internatinal Patent Application No. PCT/JP2014/084145.
Gold, Leslie I. Calreticulin: non-endoplasmic reticulum functions in physiology and disease. FAESB J, vol. 24 (3), p. 665-83, Nov. 25, 2009.
Kepp, Oliver et al., "Viral subversion of immunogenic cell death". Cell cycle, vol. 8, No. 6, pp. 860-869, 2009.
Obeid, Michel et al., "Leveraging the Immune System during Chemotherapy: Moving Calreticulin to the Cell Surface Converts Apoptotic Death from the "Silent" to Immunogenic". Cancer Research, vol. 67, No. 17, pp. 7941-7944, 2007.
Bernard-Marissal "Reduced Calreticulin Levels Link endoplasmic Reticulum Stress and Fas-Triggered Cell Death in Motoneurons Vulnerable to ALS". Journal of Neuroscience, vol. 32, No. 14, pp. 4901-4912, 2012.
Zhang, Ming et al., "Calreticulin-Stats Signaling Pathway Modulates Mitochondrial function in a Rat Model of Furazolidone-Induced Dialted Cardiomyopathy". Plos One, vol. 8, Iss. 6, pp. 66779, 2013.
Salisbury, Jeffrey L., et al., "Centrin-2 Is Required for Centriole Duplication in Mammalian Cells.", Current Biology, vol. 12, 1287-1292, (2002).
Sep. 13, 2017 Office Action issued in U.S. Appl. No. 15/164,073.
*Bradyrhizobium* sp. URHD0069, NCBI Reference Sequence: WP_029582671.1,Feb. 10, 2015, accessed on Sep. 6, 2017.
Apr. 27, 2017 Office Action issued in U.S. Appl. No. 15/164,073.
May 23, 2019 Office Action Issued in Japanese Patent Application No. 2015-554956.
Transcriptional Regulator, XRE Family [Methanocaldococcus Infernus ME], Accession No. ADG12734, GenBank [online], published Dec. 11, 2013, retrieved May 17, 2019, url: https://www.ncbi.nlm.nih.gov/protein/ADG12734.1/.

* cited by examiner

10μm

10μm

10μm

10μm

10µm

10µm

SEQUENCE LISTING

```
<160> NUMBER OF SEQ ID NOS: 78

<210> SEQ ID NO 1
<211> LENGTH: 13
<212> TYPE: PRT
<213> ORGANISM: Artificial sequence
<220> FEATURE:
<223> OTHER INFORMATION: Synthetic peptide

<400> SEQUENCE: 1

Lys Lys Arg Thr Leu Arg Lys Asn Asp Arg Lys Lys Arg
1               5                   10

<210> SEQ ID NO 2
<211> LENGTH: 8
<212> TYPE: PRT
<213> ORGANISM: Artificial sequence
<220> FEATURE:
<223> OTHER INFORMATION: Synthetic peptide

<400> SEQUENCE: 2

Trp Arg Arg Gln Ala Arg Phe Lys
1               5
```

```
<210> SEQ ID NO 3
<211> LENGTH: 11
<212> TYPE: PRT
<213> ORGANISM: Artificial sequence
<220> FEATURE:
<223> OTHER INFORMATION: Synthetic peptide

<400> SEQUENCE: 3

Tyr Gly Arg Lys Lys Arg Arg Gln Arg Arg Arg
1               5                   10

<210> SEQ ID NO 4
<211> LENGTH: 11
<212> TYPE: PRT
<213> ORGANISM: Artificial sequence
<220> FEATURE:
<223> OTHER INFORMATION: Synthetic peptide

<400> SEQUENCE: 4

Tyr Ala Arg Ala Ala Arg Gln Ala Arg Ala
1               5                   10

<210> SEQ ID NO 5
<211> LENGTH: 16
<212> TYPE: PRT
<213> ORGANISM: Artificial sequence
<220> FEATURE:
<223> OTHER INFORMATION: Synthetic peptide

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 9
<212> TYPE: PRT
<213> ORGANISM: Artificial sequence
<220> FEATURE:
<223> OTHER INFORMATION: Synthetic peptide

<400> SEQUENCE: 6

Cys Arg Ala Lys Ala Gly Asp Pro Cys
1               5

<210> SEQ ID NO 7
<211> LENGTH: 9
<212> TYPE: PRT
<213> ORGANISM: Artificial sequence
<220> FEATURE:
<223> OTHER INFORMATION: Synthetic peptide

<400> SEQUENCE: 7

Cys Glu Gln Lys Gln Glu Ile Arg Cys
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic peptide

<400> SEQUENCE: 8

Cys Gly Asn Ser Cys Ser His Cys
1               5
```

```
<210> SEQ ID NO 9
<211> LENGTH: 8
<212> TYPE: PRT
<213> ORGANISM: Artificial sequence
<220> FEATURE:
<223> OTHER INFORMATION: Synthetic peptide

<400> SEQUENCE: 9

Cys Glu Ile Ala Val His Ile Cys
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic peptide

<400> SEQUENCE: 10

Cys Lys Leu Phe Thr Cys
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic peptide

<400> SEQUENCE: 11

Cys Ala Gln Lys Gly Asn Phe Ser Cys
1               5

<210> SEQ ID NO 12
<211> LENGTH: 6
<212> TYPE: PRT
<213> ORGANISM: Artificial sequence
<220> FEATURE:
<223> OTHER INFORMATION: Synthetic peptide

<400> SEQUENCE: 12

Tyr Val Asn Ser Tyr Phe
1               5

<210> SEQ ID NO 13
<211> LENGTH: 5
<212> TYPE: PRT
<213> ORGANISM: Artificial sequence
<220> FEATURE:
<223> OTHER INFORMATION: Synthetic peptide

<400> SEQUENCE: 13

Met Thr Ala Ile Ser
1               5

<210> SEQ ID NO 14
<211> LENGTH: 6
<212> TYPE: PRT
<213> ORGANISM: Artificial sequence
<220> FEATURE:
<223> OTHER INFORMATION: Synthetic peptide

<400> SEQUENCE: 14

Cys Glu Gln Leu Phe Pro
1               5
```

```
<210> SEQ ID NO 15
<211> LENGTH: 8
<212> TYPE: PRT
<213> ORGANISM: Artificial sequence
<220> FEATURE:
<223> OTHER INFORMATION: Synthetic peptide

<400> SEQUENCE: 15

Cys Lys Gly Ser Ser Arg Ile Cys
1               5

<210> SEQ ID NO 16
<211> LENGTH: 6
<212> TYPE: PRT
<213> ORGANISM: Artificial sequence
<220> FEATURE:
<223> OTHER INFORMATION: Synthetic peptide

<400> SEQUENCE: 16

Lys Ser Trp Ser Phe Leu
1               5

<210> SEQ ID NO 17
<211> LENGTH: 6
<212> TYPE: PRT
<213> ORGANISM: Artificial sequence
<220> FEATURE:
<223> OTHER INFORMATION: Synthetic peptide

<400> SEQUENCE: 17

Asn Pro Gly Ala Ser Phe
1               5

<210> SEQ ID NO 18
<211> LENGTH: 5
<212> TYPE: PRT
<213> ORGANISM: Artificial sequence
<220> FEATURE:
<223> OTHER INFORMATION: Synthetic peptide

<400> SEQUENCE: 18

Ile Leu Glu Leu Pro
1               5

<210> SEQ ID NO 19
<211> LENGTH: 8
<212> TYPE: PRT
<213> ORGANISM: Artificial sequence
<220> FEATURE:
<223> OTHER INFORMATION: Synthetic peptide

<400> SEQUENCE: 19

Cys Phe Glu Ser Tyr Ser Asn Cys
1               5

<210> SEQ ID NO 20
<211> LENGTH: 5
<212> TYPE: PRT
<213> ORGANISM: Artificial sequence
<220> FEATURE:
<223> OTHER INFORMATION: Synthetic peptide

<400> SEQUENCE: 20

Asn Ser Ser Phe Leu
1               5
```

```
<210> SEQ ID NO 21
<211> LENGTH: 6
<212> TYPE: PRT
<213> ORGANISM: Artificial sequence
<220> FEATURE:
<223> OTHER INFORMATION: Synthetic peptide

<400> SEQUENCE: 21

Ile Arg Val Ala Phe Phe
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic peptide

<400> SEQUENCE: 22

Leu Glu Leu Ser Ser
1               5

<210> SEQ ID NO 23
<211> LENGTH: 8
<212> TYPE: PRT
<213> ORGANISM: Artificial sequence
<220> FEATURE:
<223> OTHER INFORMATION: Synthetic peptide

<400> SEQUENCE: 23

Cys Glu Glu Asn Ser Val His Cys
1               5

<210> SEQ ID NO 24
<211> LENGTH: 7
<212> TYPE: PRT
<213> ORGANISM: Artificial sequence
<220> FEATURE:
<223> OTHER INFORMATION: Synthetic peptide

<400> SEQUENCE: 24

Cys Pro Arg Cys Leu Arg Cys
1               5

<210> SEQ ID NO 25
<211> LENGTH: 6
<212> TYPE: PRT
<213> ORGANISM: Artificial sequence
<220> FEATURE:
<223> OTHER INFORMATION: Synthetic peptide

<400> SEQUENCE: 25

Phe Leu Val Ser Ile Val
1               5

<210> SEQ ID NO 26
<211> LENGTH: 5
<212> TYPE: PRT
<213> ORGANISM: Artificial sequence
<220> FEATURE:
<223> OTHER INFORMATION: Synthetic peptide

<400> SEQUENCE: 26

Ser Ser Ala Ser Trp
1               5
```

```
<210> SEQ ID NO 27
<211> LENGTH: 6
<212> TYPE: PRT
<213> ORGANISM: Artificial sequence
<220> FEATURE:
<223> OTHER INFORMATION: Synthetic peptide

<400> SEQUENCE: 27

Leu Ser Gln His Arg Gly
1               5

<210> SEQ ID NO 28
<211> LENGTH: 8
<212> TYPE: PRT
<213> ORGANISM: Artificial sequence
<220> FEATURE:
<223> OTHER INFORMATION: Synthetic peptide

<400> SEQUENCE: 28

Cys Gln Arg Lys Pro Thr Ile Cys
1               5

<210> SEQ ID NO 29
<211> LENGTH: 7
<212> TYPE: PRT
<213> ORGANISM: Artificial sequence
<220> FEATURE:
<223> OTHER INFORMATION: Synthetic peptide

<400> SEQUENCE: 29

Cys Lys Gly Asn Gln Gln Cys
1               5

<210> SEQ ID NO 30
<211> LENGTH: 7
<212> TYPE: PRT
<213> ORGANISM: Artificial sequence
<220> FEATURE:
<223> OTHER INFORMATION: Synthetic peptide

<400> SEQUENCE: 30

Cys Lys Glu Thr Asn Asn Cys
1               5

<210> SEQ ID NO 31
<211> LENGTH: 6
<212> TYPE: PRT
<213> ORGANISM: Artificial sequence
<220> FEATURE:
<223> OTHER INFORMATION: Synthetic peptide

<400> SEQUENCE: 31

Leu Leu Leu Val Ser Phe
1               5

<210> SEQ ID NO 32
<211> LENGTH: 6
<212> TYPE: PRT
<213> ORGANISM: Artificial sequence
<220> FEATURE:
<223> OTHER INFORMATION: Synthetic peptide

<400> SEQUENCE: 32

Tyr Cys Trp Phe Pro Leu
1               5
```

```
<210> SEQ ID NO 33
<211> LENGTH: 5
<212> TYPE: PRT
<213> ORGANISM: Artificial sequence
<220> FEATURE:
<223> OTHER INFORMATION: Synthetic peptide

<400> SEQUENCE: 33

Ile Val Gly Phe Leu
1               5

<210> SEQ ID NO 34
<211> LENGTH: 9
<212> TYPE: PRT
<213> ORGANISM: Artificial sequence
<220> FEATURE:
<223> OTHER INFORMATION: Synthetic peptide

<400> SEQUENCE: 34

Cys Leu Ser Lys Gly Asn Thr Ser Cys
1               5

<210> SEQ ID NO 35
<211> LENGTH: 9
<212> TYPE: PRT
<213> ORGANISM: Artificial sequence
<220> FEATURE:
<223> OTHER INFORMATION: Synthetic peptide

<400> SEQUENCE: 35

Cys Leu Thr Lys Gly Asn Thr Ser Cys
1               5

<210> SEQ ID NO 36
<211> LENGTH: 9
<212> TYPE: PRT
<213> ORGANISM: Artificial sequence
<220> FEATURE:
<223> OTHER INFORMATION: Synthetic peptide

<400> SEQUENCE: 36

Cys Leu Thr Lys Ala Asn Thr Ser Cys
1               5

<210> SEQ ID NO 37
<211> LENGTH: 7
<212> TYPE: PRT
<213> ORGANISM: Artificial sequence
<220> FEATURE:
<223> OTHER INFORMATION: Synthetic peptide

<400> SEQUENCE: 37

Cys Gln Gln Gly Ser Leu Cys
1               5

<210> SEQ ID NO 38
<211> LENGTH: 8
<212> TYPE: PRT
<213> ORGANISM: Artificial sequence
<220> FEATURE:
<223> OTHER INFORMATION: Synthetic peptide

<400> SEQUENCE: 38

Cys Asn Lys Asp Glu Val Tyr Cys
1               5
```

```
<210> SEQ ID NO 39
<211> LENGTH: 7
<212> TYPE: PRT
<213> ORGANISM: Artificial sequence
<220> FEATURE:
<223> OTHER INFORMATION: Synthetic peptide

<400> SEQUENCE: 39

Cys Thr Arg Met Lys Ser Cys
1               5

<210> SEQ ID NO 40
<211> LENGTH: 8
<212> TYPE: PRT
<213> ORGANISM: Artificial sequence
<220> FEATURE:
<223> OTHER INFORMATION: Synthetic peptide

<400> SEQUENCE: 40

Cys Ile Asp Phe Ile Leu Val Cys
1               5

<210> SEQ ID NO 41
<211> LENGTH: 7
<212> TYPE: PRT
<213> ORGANISM: Artificial sequence
<220> FEATURE:
<223> OTHER INFORMATION: Synthetic peptide

<400> SEQUENCE: 41

Cys Thr Ser Ser Leu Leu Cys
1               5

<210> SEQ ID NO 42
<211> LENGTH: 6
<212> TYPE: PRT
<213> ORGANISM: Artificial sequence
<220> FEATURE:
<223> OTHER INFORMATION: Synthetic peptide

<400> SEQUENCE: 42

Tyr Gly Val Ser Ser Leu
1               5

<210> SEQ ID NO 43
<211> LENGTH: 5
<212> TYPE: PRT
<213> ORGANISM: Artificial sequence
<220> FEATURE:
<223> OTHER INFORMATION: Synthetic peptide

<400> SEQUENCE: 43

Met Glu Val Leu Phe
1               5

<210> SEQ ID NO 44
<211> LENGTH: 6
<212> TYPE: PRT
<213> ORGANISM: Artificial sequence
<220> FEATURE:
<223> OTHER INFORMATION: Synthetic peptide

<400> SEQUENCE: 44

Trp Thr Glu Phe Ser Ser
1               5
```

```
<210> SEQ ID NO 45
<211> LENGTH: 12
<212> TYPE: PRT
<213> ORGANISM: Artificial sequence
<220> FEATURE:
<223> OTHER INFORMATION: Synthetic peptide

<400> SEQUENCE: 45

Phe Thr Thr Ser Asn His Thr Ser Arg His Gly Ser
1               5                   10

<210> SEQ ID NO 46
<211> LENGTH: 12
<212> TYPE: PRT
<213> ORGANISM: Artificial sequence
<220> FEATURE:
<223> OTHER INFORMATION: Synthetic peptide

<400> SEQUENCE: 46

Ser Val Ser Val Gly Met Lys Pro Ser Pro Arg Pro
1               5                   10

<210> SEQ ID NO 47
<211> LENGTH: 12
<212> TYPE: PRT
<213> ORGANISM: Artificial sequence
<220> FEATURE:
<223> OTHER INFORMATION: Synthetic peptide

<400> SEQUENCE: 47

Gly Pro His Leu Gly Met Asn Gln Arg Arg Arg Pro
1               5                   10

<210> SEQ ID NO 48
<211> LENGTH: 12
<212> TYPE: PRT
<213> ORGANISM: Artificial sequence
<220> FEATURE:
<223> OTHER INFORMATION: Synthetic peptide

<400> SEQUENCE: 48

Gly Pro His His Tyr Trp Tyr His Leu Arg Leu Pro
1               5                   10

<210> SEQ ID NO 49
<211> LENGTH: 12
<212> TYPE: PRT
<213> ORGANISM: Artificial sequence
<220> FEATURE:
<223> OTHER INFORMATION: Synthetic peptide

<400> SEQUENCE: 49

Gly Ala Val Thr Tyr Ser Arg Ile Ser Gly Gln Tyr
1               5                   10

<210> SEQ ID NO 50
<211> LENGTH: 12
<212> TYPE: PRT
<213> ORGANISM: Artificial sequence
<220> FEATURE:
<223> OTHER INFORMATION: Synthetic peptide

<400> SEQUENCE: 50

Ser Leu Leu Pro His Ser Asn His Ala Lys His Tyr
1               5                   10
```

```
<210> SEQ ID NO 51
<211> LENGTH: 12
<212> TYPE: PRT
<213> ORGANISM: Artificial sequence
<220> FEATURE:
<223> OTHER INFORMATION: Synthetic peptide

<400> SEQUENCE: 51

Thr Pro Ser Leu Pro Pro Thr Met Phe Arg Leu Thr
1               5                   10

<210> SEQ ID NO 52
<211> LENGTH: 12
<212> TYPE: PRT
<213> ORGANISM: Artificial sequence
<220> FEATURE:
<223> OTHER INFORMATION: Synthetic peptide

<400> SEQUENCE: 52

Gln Ser Pro Val Asn His His Tyr His Tyr His Ile
1               5                   10

<210> SEQ ID NO 53
<211> LENGTH: 12
<212> TYPE: PRT
<213> ORGANISM: Artificial sequence
<220> FEATURE:
<223> OTHER INFORMATION: Synthetic peptide

<400> SEQUENCE: 53

Asn Met Thr Thr Tyr Pro Met His Asn Asn Thr Val
1               5                   10

<210> SEQ ID NO 54
<211> LENGTH: 12
<212> TYPE: PRT
<213> ORGANISM: Artificial sequence
<220> FEATURE:
<223> OTHER INFORMATION: Synthetic peptide

<400> SEQUENCE: 54

Glu Phe Glu Tyr Phe His Pro Ala Thr Phe Arg Leu
1               5                   10

<210> SEQ ID NO 55
<211> LENGTH: 9
<212> TYPE: PRT
<213> ORGANISM: Artificial sequence
<220> FEATURE:
<223> OTHER INFORMATION: Synthetic peptide

<400> SEQUENCE: 55

Cys Leu Ala Pro Ser Pro Ser Lys Cys
1               5

<210> SEQ ID NO 56
<211> LENGTH: 9
<212> TYPE: PRT
<213> ORGANISM: Artificial sequence
<220> FEATURE:
<223> OTHER INFORMATION: Synthetic peptide

<400> SEQUENCE: 56

Cys Ser Ser Ala Thr Gly Lys Ser Cys
1               5
```

```
<210> SEQ ID NO 57
<211> LENGTH: 9
<212> TYPE: PRT
<213> ORGANISM: Artificial sequence
<220> FEATURE:
<223> OTHER INFORMATION: Synthetic peptide

<400> SEQUENCE: 57

Cys Leu Gly Gln Thr Lys Met Arg Cys
1               5

<210> SEQ ID NO 58
<211> LENGTH: 9
<212> TYPE: PRT
<213> ORGANISM: Artificial sequence
<220> FEATURE:
<223> OTHER INFORMATION: Synthetic peptide

<400> SEQUENCE: 58

Cys Gly His Arg Pro Tyr Gln Tyr Cys
1               5

<210> SEQ ID NO 59
<211> LENGTH: 9
<212> TYPE: PRT
<213> ORGANISM: Artificial sequence
<220> FEATURE:
<223> OTHER INFORMATION: Synthetic peptide

<400> SEQUENCE: 59

Cys Trp Ala Phe Pro Leu His His Cys
1               5

<210> SEQ ID NO 60
<211> LENGTH: 9
<212> TYPE: PRT
<213> ORGANISM: Artificial sequence
<220> FEATURE:
<223> OTHER INFORMATION: Synthetic peptide

<400> SEQUENCE: 60

Cys Thr Leu Asn Ser His Ser Asn Cys
1               5

<210> SEQ ID NO 61
<211> LENGTH: 9
<212> TYPE: PRT
<213> ORGANISM: Artificial sequence
<220> FEATURE:
<223> OTHER INFORMATION: Synthetic peptide

<400> SEQUENCE: 61

Cys Glu Ile Ser Ala Lys Arg Thr Cys
1               5

<210> SEQ ID NO 62
<211> LENGTH: 9
<212> TYPE: PRT
<213> ORGANISM: Artificial sequence
<220> FEATURE:
<223> OTHER INFORMATION: Synthetic peptide

<400> SEQUENCE: 62

Cys His Ile Leu His Ala Gln Ala Cys
1               5
```

-continued

```
<210> SEQ ID NO 63
<211> LENGTH: 9
<212> TYPE: PRT
<213> ORGANISM: Artificial sequence
<220> FEATURE:
<223> OTHER INFORMATION: Synthetic peptide

<400> SEQUENCE: 63

Gly Pro Arg Pro Pro Ser Leu Glu Cys
1               5

<210> SEQ ID NO 64
<211> LENGTH: 9
<212> TYPE: PRT
<213> ORGANISM: Artificial sequence
<220> FEATURE:
<223> OTHER INFORMATION: Synthetic peptide

<400> SEQUENCE: 64

Cys Thr Gly His Trp Ala Ser Glu Cys
1               5

<210> SEQ ID NO 65
<211> LENGTH: 9
<212> TYPE: PRT
<213> ORGANISM: Artificial sequence
<220> FEATURE:
<223> OTHER INFORMATION: Synthetic peptide

<400> SEQUENCE: 65

Cys Ser Tyr Glu Lys Arg Pro Met Cys
1               5

<210> SEQ ID NO 66
<211> LENGTH: 9
<212> TYPE: PRT
<213> ORGANISM: Artificial sequence
<220> FEATURE:
<223> OTHER INFORMATION: Synthetic peptide

<400> SEQUENCE: 66

Cys Leu Thr Lys Ser Tyr Thr Ser Cys
1               5

<210> SEQ ID NO 67
<211> LENGTH: 15
<212> TYPE: PRT
<213> ORGANISM: Artificial sequence
<220> FEATURE:
<223> OTHER INFORMATION: Synthetic peptide

<400> SEQUENCE: 67

Gly Ala Ala Pro Pro Gly Gln Lys Gly Gln Ala Asn Ala Thr Arg
1               5                   10                  15

<210> SEQ ID NO 68
<211> LENGTH: 7
<212> TYPE: PRT
<213> ORGANISM: Artificial sequence
<220> FEATURE:
<223> OTHER INFORMATION: Synthetic peptide

<400> SEQUENCE: 68

Val Gln Ile Ile Asn Lys Lys
1               5
```

```
<210> SEQ ID NO 69
<211> LENGTH: 17
<212> TYPE: PRT
<213> ORGANISM: Artificial sequence
<220> FEATURE:
<223> OTHER INFORMATION: Synthetic peptide

<400> SEQUENCE: 69

Ile Gly Ser Leu Asp Asn Ile Thr His Val Pro Gly Gly Gly Asn Lys
1               5                   10                  15

Lys

<210> SEQ ID NO 70
<211> LENGTH: 11
<212> TYPE: PRT
<213> ORGANISM: Artificial sequence
<220> FEATURE:
<223> OTHER INFORMATION: Synthetic peptide

<400> SEQUENCE: 70

Lys Val Gln Ile Ile Asn Lys Lys Leu Asp Leu
1               5                   10

<210> SEQ ID NO 71
<211> LENGTH: 11
<212> TYPE: PRT
<213> ORGANISM: Artificial sequence
<220> FEATURE:
<223> OTHER INFORMATION: Synthetic peptide

<400> SEQUENCE: 71

Ser Val Gln Ile Val Tyr Lys Pro Val Asp Leu
1               5                   10

<210> SEQ ID NO 72
<211> LENGTH: 6
<212> TYPE: PRT
<213> ORGANISM: Artificial sequence
<220> FEATURE:
<223> OTHER INFORMATION: Synthetic peptide

<400> SEQUENCE: 72

Val Gln Ile Val Tyr Lys
1               5

<210> SEQ ID NO 73
<211> LENGTH: 17
<212> TYPE: PRT
<213> ORGANISM: Artificial sequence
<220> FEATURE:
<223> OTHER INFORMATION: Synthetic peptide

<400> SEQUENCE: 73

Met Leu Pro Ser Leu Ala Leu Leu Leu Leu Ala Ala Trp Thr Val Arg
1               5                   10                  15

Ala

<210> SEQ ID NO 74
<211> LENGTH: 17
<212> TYPE: PRT
<213> ORGANISM: Artificial sequence
<220> FEATURE:
<223> OTHER INFORMATION: Synthetic peptide
```

```
<400> SEQUENCE: 74

Met Leu Pro Gly Leu Ala Leu Leu Leu Ala Ala Trp Thr Ala Arg
1               5                   10                  15

Ala

<210> SEQ ID NO 75
<211> LENGTH: 22
<212> TYPE: PRT
<213> ORGANISM: Artificial sequence
<220> FEATURE:
<223> OTHER INFORMATION: Synthetic peptide

<400> SEQUENCE: 75

Lys Lys Arg Thr Leu Arg Lys Asn Asp Arg Lys Lys Arg Cys Arg Ala
1               5                   10                  15

Lys Ala Gly Asp Pro Cys
            20

<210> SEQ ID NO 76
<211> LENGTH: 19
<212> TYPE: PRT
<213> ORGANISM: Artificial sequence
<220> FEATURE:
<223> OTHER INFORMATION: Synthetic peptide

<400> SEQUENCE: 76

Lys Lys Arg Thr Leu Arg Lys Asn Asp Arg Lys Lys Arg Asn Pro Gly
1               5                   10                  15

Ala Ser Phe

<210> SEQ ID NO 77
<211> LENGTH: 22
<212> TYPE: PRT
<213> ORGANISM: Artificial sequence
<220> FEATURE:
<223> OTHER INFORMATION: Synthetic peptide

<400> SEQUENCE: 77

Lys Lys Arg Thr Leu Arg Lys Asn Asp Arg Lys Lys Arg Gly Pro Arg
1               5                   10                  15

Pro Pro Ser Leu Glu Cys
            20

<210> SEQ ID NO 78
<211> LENGTH: 12
<212> TYPE: PRT
<213> ORGANISM: Artificial sequence
<220> FEATURE:
<223> OTHER INFORMATION: Synthetic peptide

<400> SEQUENCE: 78

Leu Ala Ala Arg Ala Val Arg Phe Ser Glu Lys Val
1               5                   10
```

METHOD FOR PROMOTING EXPRESSION OF CALRETICULIN, AND SYNTHETIC PEPTIDE FOR USE IN METHOD FOR PROMOTING EXPRESSION OF CALRETICULIN

This application is a National Phase of International Application No. PCT/JP202014/084145 filed on Dec. 14, 2014, which claims priority to Japanese Patent Application No. 2013-270470 submitted on Dec. 26, 2013. The entire content of that Japanese application is herein incorporated by reference.

TECHNICAL FIELD

The present invention relates to a method for promoting expression of the calreticulin protein in at least one kind of eukaryotic cell, and to a synthetic peptide for use in this method. The present invention also relates to a composition having this synthetic peptide as an active ingredient.

BACKGROUND ART

Calreticulin is localized in the lumen of the endoplasmic reticulum (ER), and is known as a chaperone protein involved in qualitative control, folding and the like of newly synthesized proteins (including glycoproteins). It is also known to play an important role in maintaining and regulating calcium concentrations within the cytoplasm and the endoplasmic reticulum. Because heart formation is inhibited in mice lacking the calreticulin gene, leading to embryonic death, calreticulin appears to play an important role in vivo.

In recent years, it has become clear that calreticulin occurs not only in the lumen of the endoplasmic reticulum, but also in the cytoplasm, cell surface, extracellular fractions and the like, and is involved in a variety of important biological processes, namely cell adhesion, cellular chemotaxis, cell proliferation and antigen presentation in acquired immunity (Non Patent Literature 1). For example, it has been reported in Non Patent Literature 2 and 3 that in abnormal cells (cancer cells and cells infected with pathogens), expression of calreticulin is promoted as an immune activating protein (so-called "eat-me signal") on the surfaces of these cells (typically, on the cell membranes) when they undergo immunogenic cell death.

It is becoming clear that expression of calreticulin in locations other than the ER (such as on the cell surface or outside the cell) is associated with various diseases. For example, associations have been reported between extrareticular calreticulin expression and amyotrophic lateral sclerosis (ALS), dilated cardiomyopathy, Alzheimer's disease and various immune conditions (for example, inflammatory bowel disease, rheumatoid arthritis, systemic lupus erythematosus and the like) (Non Patent Literature 1, 4, 5).

CITATION LIST

Patent Literature

[Patent Literature 1] WO 2009/093692

Non Patent Literature

[Non Patent Literature 1] The FASEB Journal, Vol. 24 (No. 3), 2010, pp. 665-683
[Non Patent Literature 2] Cell Cycle, Vol. 8 (No. 6), 2009, pp. 860-869
[Non Patent Literature 3] Cancer Research, Vol. 67 (No. 17), 2007, pp. 7941-7944
[Non Patent Literature 4] The Journal of Neuroscience, Vol. 32 (No. 14), 2012, pp. 4901-4912
[Non Patent Literature 5] PLOS ONE, Vol. 8 (No. 6), 2013, e66779

SUMMARY OF INVENTION

As discussed above, calreticulin plays an important role in vivo. If the expressed amount of calreticulin could be regulated, this might be a first step towards treating diseases associated with abnormal calreticulin expression. For example, by promoting calreticulin expression, it might be possible to prevent (or suppress) undesirable physiological effects caused by insufficient expression of calreticulin. Alternatively, by promoting expression of the calreticulin that is expressed on the surfaces of abnormal cells in vivo, it might be possible to eliminate abnormal cells at a high rate because immune cells recognize calreticulin as an eat-me signal. Moreover, promotion of calreticulin expression on the cell surfaces of abnormal cells is a potential way of clearly distinguishing normal cells from abnormal cells, and could be used to sort cells in vitro.

Conventionally, however, there has been no method or agent for easily and efficiently promoting calreticulin expression. Therefore, the present invention was created with the object of providing a method for promoting calreticulin expression in at least one kind of eukaryote, together with a synthetic peptide used in this method. Another object is to provide a composition (pharmaceutical composition) having such a peptide as an active ingredient.

The inventors and others focused on proteins (hereunder sometimes called spindle formation-associated proteins) associated with formation and maintenance of spindles. We then synthesized synthetic peptides containing amino acid sequences (hereunder sometimes called siRNA-associated sequences) translated from RNA sequences constituting the siRNA (small interfering RNA) of genes (DNA sequences) coding for the amino acid sequences of various spindle formation-associated proteins. It was discovered that when supplied to target eukaryotic cells (typically, when supplied to medium in which such cells are cultured), especially various tumor cells, stem cells or neural cells (for example, neurons, astrocytes, oligodendrocytes, etc.) and particularly genomically unstable cells (in other words, abnormal cells), these synthetic peptides have the ability (calreticulin expression-promoting ability) to potentially promote calreticulin expression or increase the expressed amount of calreticulin in these cells.

The inventors also focused on a number of peptides (peptides capable of functioning as FtsZ inhibitors or FtsA inhibitors), isolated by ordinary phage display methods, as peptides that inhibit the activity (GTPase activity of FtsZ protein or ATPase activity of FtsA protein) of two proteins present in prokaryotic bacterial cells: filamenting temperature-sensitive mutant Z (FtsZ), which is the protein component of a protein structure called the Z-ring that is involved in bacterial cell division, and filamenting temperature-sensitive mutant A (FtsA), which is known to function as an anchor that binds to the C-terminus of the FtsZ protein and anchors the FtsZ protein to the cell membrane. Synthetic peptides constructed so as to include such peptides capable of functioning as FtsZ inhibitors and FtsA inhibitors have also been found to have calreticulin expression-promoting ability.

The inventors also focused on proteins associated with cell division (that is, cell division proteins). Synthetic peptides constructed so as to include partial amino acid sequences of cell division proteins, or specifically partial amino acid sequences of a group of microtubule-associated proteins (MAP: proteins that bind to microtubules, specifically tubulin) called tau proteins (t proteins), or more specifically amino acid sequences comprising partial amino acid sequences of regions associated with binding between tau proteins and microtubules (tubulin) in the amino acid sequences of tau proteins, were also found to have calreticulin expression-promoting activity.

The inventors also focused on signal peptides in amyloid precursor proteins (APP). Synthetic peptides constructed so as to include amino acid sequences constituting signal peptides of APP proteins were also found to have calreticulin expression-promoting activity.

The inventors perfected the present invention based on these findings.

To achieve these objects, the present invention provides a synthetic peptide (hereunder sometimes called a "calreticulin expression-promoting peptide") for use in promoting calreticulin expression in at least one kind of eukaryotic cells (preferably, for increasing the amount of calreticulin on the cell surfaces (typically, the cell membrane surfaces) of target cells).

As such a peptide, the invention provides a synthetic peptide having a calreticulin expression-promoting peptide sequence comprising an amino acid sequence represented by any of SEQ ID NOs: 6 to 74, or a modified amino acid sequence formed by substitution, deletion and/or addition of 1, 2 or 3 amino acid residues in any of these amino acid sequences.

The calreticulin expression-promoting peptide disclosed here can be easily manufactured artificially by chemical synthesis (or biosynthesis). Because the substance itself has a simple structure (linear peptide chain), it is easy to handle, and for example calreticulin expression can be promoted in a target cell (preferably, the amount of calreticulin present on the cell surface of a target cell (typically, the surface of the cell membrane) can be increased) by the simple operation of supplying the calreticulin expression-promoting peptide to the target cell (typically, to medium of the cell culture).

Of the amino acid sequences represented by SEQ ID NOs: 6 to 72, the amino acid sequences of SEQ ID NOs: 6 to 44 are siRNA-associated sequences of spindle formation-associated proteins. The amino acid sequences of SEQ ID NOs: 45 to 66 are amino acid sequences of peptides that may function as FtsZ inhibitors or FtsA inhibitors. The amino acid sequences of SEQ ID NOs: 67 to 72 are partial amino acid sequences of cell division proteins (typically, tau proteins). The amino acid sequences of SEQ ID NOs: 73 and 74 are amino acid sequences constituting APP signal peptides. Synthetic peptides having these amino acid sequences are artificially designed synthetic peptides that do not exist by themselves in the natural world, and produce excellent calreticulin expression-promoting activity. In particular, these synthetic peptides exhibit strong calreticulin expression-promoting activity in human-derived cells. Of these, the synthetic peptides having the amino acid sequences of SEQ ID NOs: 6, 8, 17, 28, 63, 68, 69 and 73 exhibit particularly strong calreticulin expression-promoting activity.

The cells targeted by the calreticulin expression-promoting peptide disclosed here are preferably tumor cells, stem cells or neural cells (for example, astrocytes, neurons, oligodendrocytes or the like) from humans or non-human mammals.

The calreticulin expression-promoting peptide disclosed here exhibits strong calreticulin expression-promoting activity in these cells (tumor cells, stem cells, neural cells), and especially in these cells when derived from humans. Such a synthetic peptide is extremely useful in the medical industries.

A preferred embodiment of the calreticulin expression-promoting peptide disclosed here has a transmembrane peptide sequence at the N-end or C-end of the calreticulin expression-promoting peptide sequence.

Having such a transmembrane peptide sequence, the calreticulin expression-promoting peptide can be used favorably for implementing the invention because the calreticulin expression-promoting peptide sequence can be efficiently introduced into a cell (inside the cell membrane and/or nuclear membrane).

Moreover, a preferred embodiment of the calreticulin expression-promoting peptide disclosed here has the following amino acid sequence:

KKRTLRKNDRKKR (SEQ ID NO: 1)

as the transmembrane peptide sequence.

The amino acid sequence represented by SEQ ID NO: 1 is a typical example of an amino acid sequence constituting a transmembrane peptide, and can efficiently promote calreticulin expression in a target cell.

Moreover, in a preferred embodiment of the calreticulin expression-promoting peptide disclosed here the total number of amino acid residues constituting the synthetic peptide is 50 or fewer.

A peptide with such a short peptide chain can be used favorably for implementing the invention because it is easy to chemically synthesize, and is also inexpensive and easy to handle.

Moreover, a preferred embodiment of the calreticulin expression-promoting peptide disclosed here can promote the movement of calreticulin from inside the cell (typically, inside the ER) to the cell surface (typically, the surface of the cell membrane). Thus, it can increase the amount of calreticulin present on the surface of the cell membrane.

As a result, with the peptide of this embodiment it is possible to increase the effect of calreticulin as an eat-me signal recognized by immune cells by increasing the amount of calreticulin present on the cell membrane. Alternatively, cells with high calreticulin expression can be distinguished using this calreticulin as an indicator.

Another aspect of the present invention provides a calreticulin expression promoter (pharmaceutical composition) for use in promoting expression of calreticulin in at least one kind of eukaryotic cell, containing the calreticulin expression-promoting peptide disclosed here as an active ingredient.

Typically, this calreticulin expression promoter also contains at least one kind of pharmaceutically acceptable carrier (such as at least one kind of base contributing to improved stability of the peptide, or a liquid medium such as saline or various kinds of buffers).

Because this calreticulin expression promoter contains a synthetic peptide with a simple structure (linear chain) as an active ingredient, expression of calreticulin in a target cell can be promoted for example by the simple operation of supplying the calreticulin expression promoter to the target cell (typically, to medium of the cell culture). In particular, the calreticulin expression promoter disclosed here can effectively promote calreticulin expression in various tumor cells, stem cells and neural cells (for example, neurons, astrocytes and oligodendrocytes), and especially in genomically unstable cells (that is, abnormal cells). Moreover, because the active ingredient is a synthetic peptide can easily be manufactured artificially by chemical synthesis (or biosynthesis), the desired amount of the calreticulin expression promoter can be easily prepared.

Yet another aspect of the present invention provides a method for promoting the expression of calreticulin in at least one kind of eukaryotic cell, this method including: preparing a cell culture containing the target eukaryotic cell; supplying at least once to the cell culture the calreticulin expression-promoting peptide disclosed here; and culturing for a specified amount of time the cell culture to which the peptide has been supplied at least once.

With this in vitro calreticulin expression-promoting method, calreticulin expression can be promoted in target cells by the simple operation of supplying a synthetic peptide with a simple structure as discussed above to target cells (typically, to medium of the cell culture). In particular, this method can promote calreticulin expression in various tumor cells, stem cells and neural cells (for example, neurons, astrocytes and oligodendrocytes), and especially in genomically unstable cells (that is, abnormal cells).

Thus, with the present invention it is possible to use the calreticulin expression-promoting peptide (that is, the calreticulin expression promoter) disclosed here to manufacture a cell culture containing cells having high calreticulin expression. In other words, the invention provides a method for manufacturing a cell culture containing cells with high calreticulin expression, encompassing the calreticulin expression promotion method disclosed here.

DESCRIPTION OF EMBODIMENTS

Figure 1:
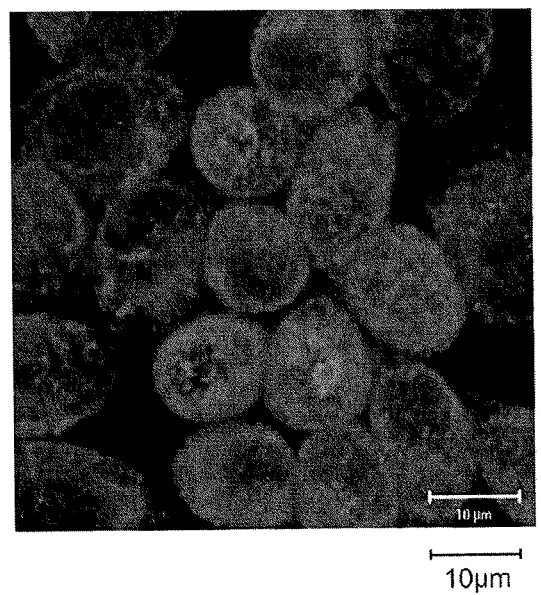
FIG. 1 is a fluorescence micrograph (image) examining the calreticulin expression state of HeLaS3 cells cultured after addition of a calreticulin expression-promoting peptide (Sample 1) of one embodiment to those HeLaS3 cells.
Figure 2:
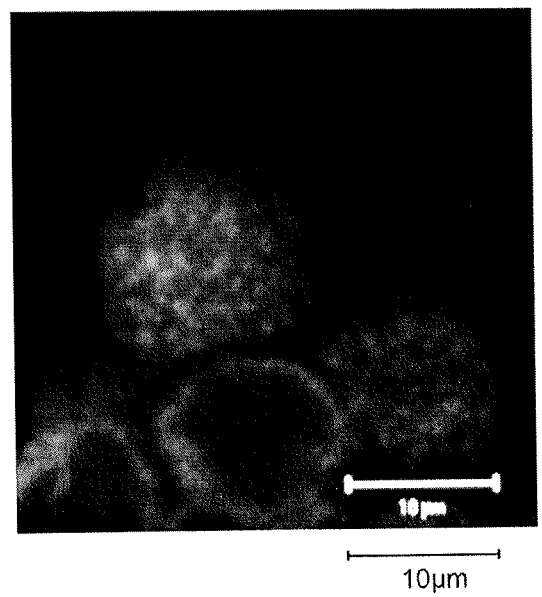
FIG. 2 is a fluorescence micrograph (image) examining the calreticulin expression state of HeLaS3 cells cultured after addition of a calreticulin expression-promoting peptide (Sample 2) of one embodiment to those HeLaS3 cells.
Figure 3:
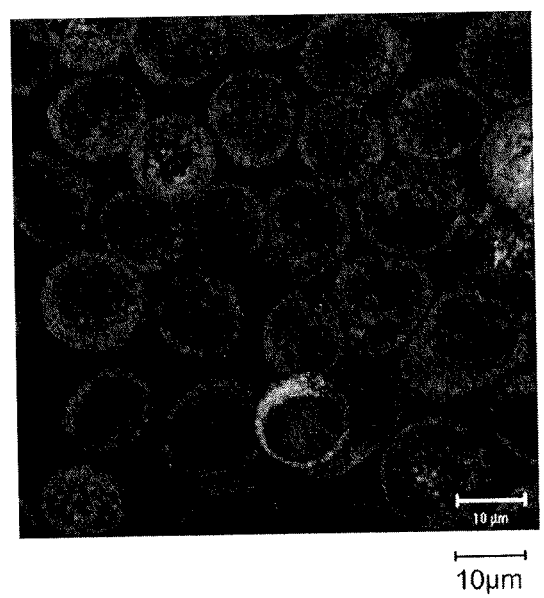
FIG. 3 is a fluorescence micrograph (image) examining the calreticulin expression state of HeLaS3 cells cultured after addition of a calreticulin expression-promoting peptide (Sample 3) of one embodiment to those HeLaS3 cells.
Figure 4:
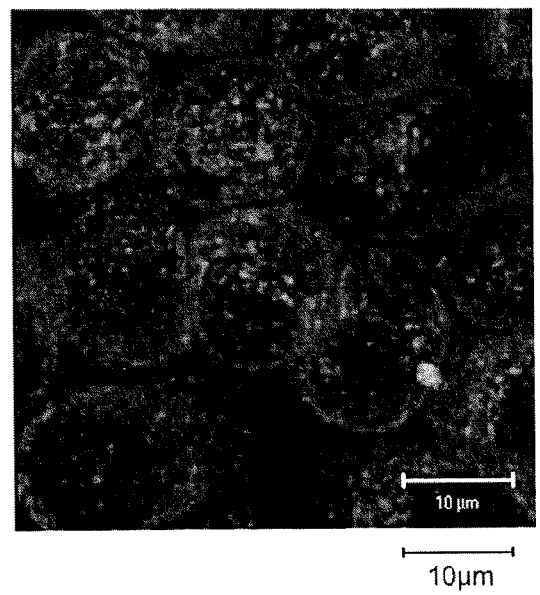
FIG. 4 is a fluorescence micrograph (image) examining the calreticulin expression state of HeLaS3 cells cultured after addition of a calreticulin expression-promoting peptide (Sample 4) of one embodiment to those HeLaS3 cells.
Figure 5:
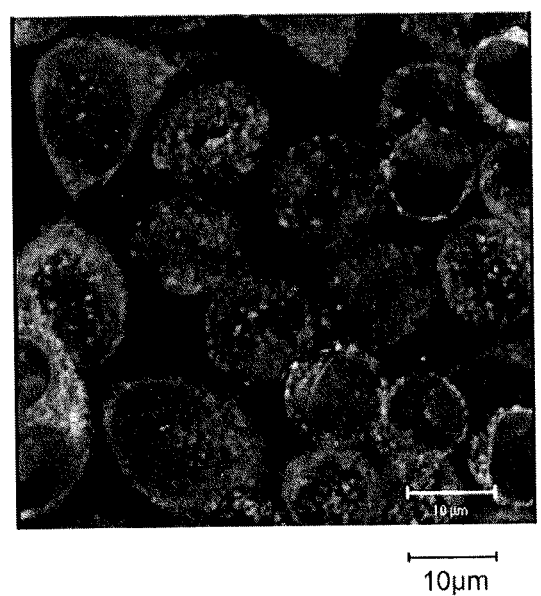
FIG. 5 is a fluorescence micrograph (image) examining the calreticulin expression state of HeLaS3 cells cultured after addition of a calreticulin expression-promoting peptide (Sample 5) of one embodiment to those HeLaS3 cells.
Figure 6:
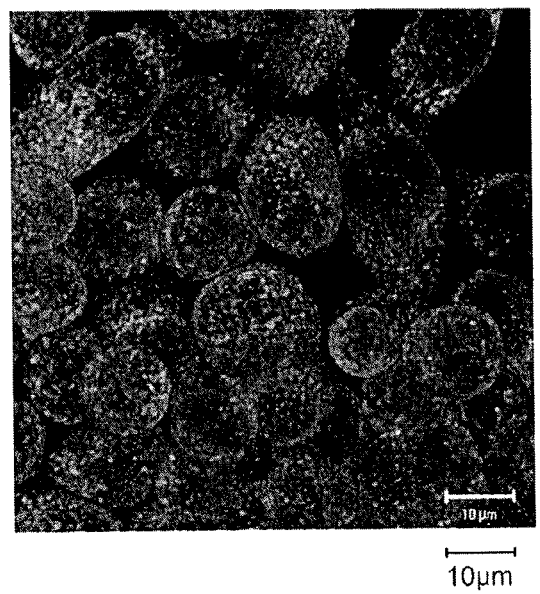
FIG. 6 is a fluorescence micrograph (image) examining the calreticulin expression state of HeLaS3 cells cultured after addition of a calreticulin expression-promoting peptide (Sample 6) of one embodiment to those HeLaS3 cells.
Figure 7:
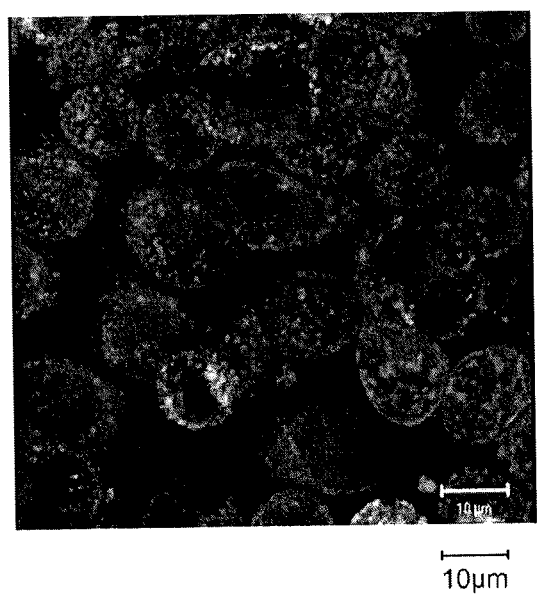
FIG. 7 is a fluorescence micrograph (image) examining the calreticulin expression state of HeLaS3 cells cultured after addition of a calreticulin expression-promoting peptide (Sample 7) of one embodiment to those HeLaS3 cells.
Figure 8:
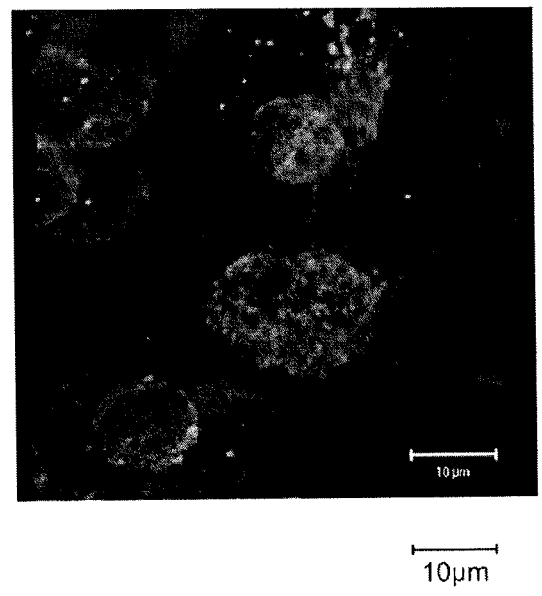
FIG. 8 is a fluorescence micrograph (image) examining the calreticulin expression state of HeLaS3 cells cultured after addition of a calreticulin expression-promoting peptide (Sample 8) of one embodiment to those HeLaS3 cells.
Figure 9:
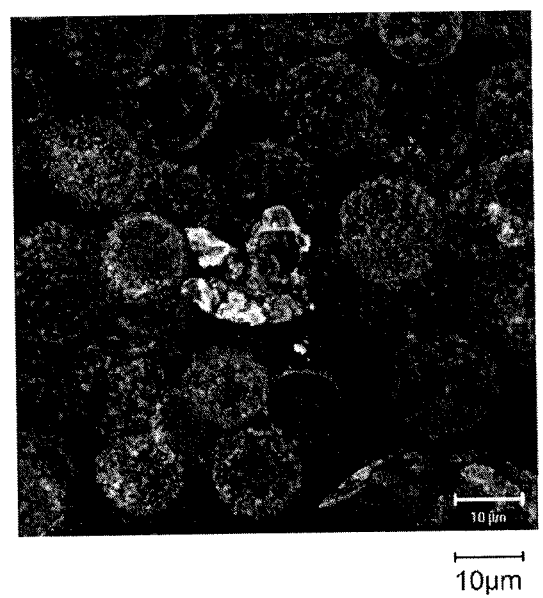
FIG. 9 is a fluorescence micrograph (image) examining the calreticulin expression state of HeLaS3 cells cultured after addition of a calreticulin expression-promoting peptide (Sample 9) of one embodiment to those HeLaS3 cells.
Figure 10:
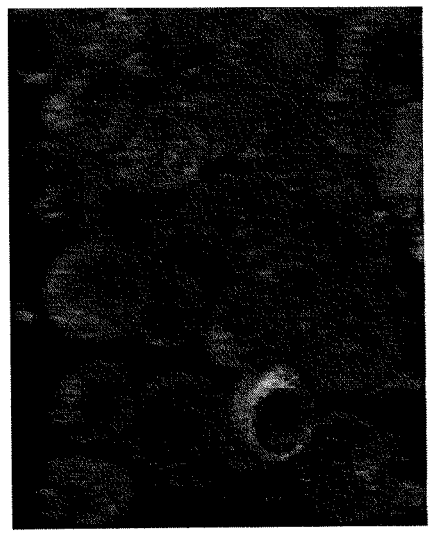
FIG. 10 is a fluorescence micrograph (image) examining the calreticulin expression state of HeLaS3 cells cultured after addition of a calreticulin expression-promoting peptide (Sample 10) of one embodiment to those HeLaS3 cells.
Figure 11:
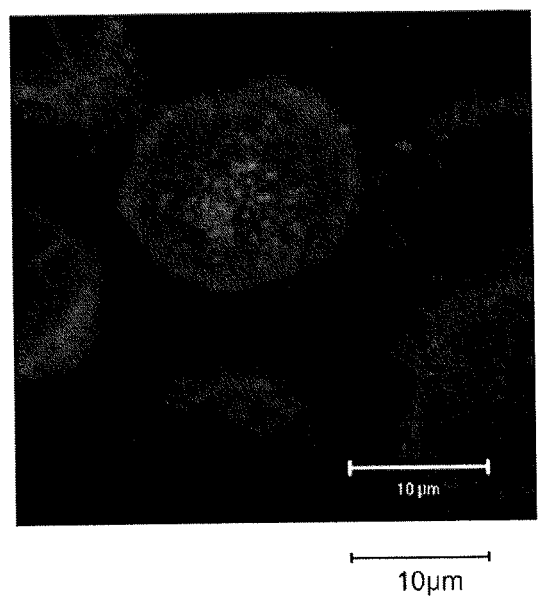
FIG. 11 is a fluorescence micrograph (image) examining the calreticulin expression state of HeLaS3 cells cultured after addition of a calreticulin expression-promoting peptide (Sample 11) of one embodiment to those HeLaS3 cells.
Figure 12:
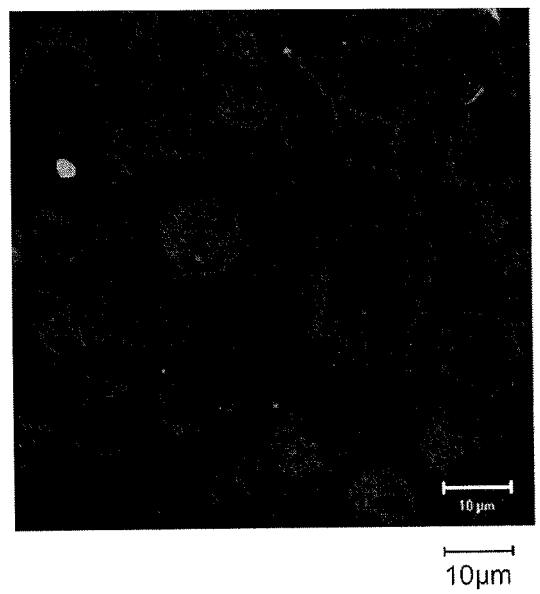
FIG. 12 is a fluorescence micrograph (image) examining the calreticulin expression state of HeLaS3 cells cultured after addition of a synthetic peptide (Sample 12) constructed from a random combination of amino acid residues as a comparative example to those HeLaS3 cells.

Preferred embodiments of the invention are explained below. Matters other than those explicitly mentioned in this Description (such as the primary structure and chain length of the synthetic peptide disclosed here) that are necessary for implementing the invention (for example, chemical synthesis methods, cell culture techniques, and ordinary matters related to preparing a pharmaceutically composition with the peptide as a component) can be understood as design matters by a person skilled in the art based on conventional technology in the fields of cell engineering, physiology, medicine, pharmacology, organic chemistry, biochemistry, genetic engineering, protein engineering, molecular biology, genetics and the like. The invention can be implemented based on the content disclosed in this Description and technical common knowledge in these fields. In the explanations below, amino acids are in some cases represented by one-letter designations in accordance with the nomenclature for amino acids given in the IUPAC-IUB guidelines (but 3-letter designations are used in the sequence tables).

Moreover, the entire content of all of the literature cited in this Description is herein incorporated by reference.

In this Description, a "synthetic peptide" is a peptide fragment that has been manufactured by artificial chemical synthesis or biosynthesis (that is, produced based on genetic engineering), and that can exist stably in a specific composition (such as a calreticulin expression promoter).

In this Description, moreover, the term "peptide" refers to an amino acid polymer having multiple peptide bonds, with no restriction on the number of amino acid residues in the peptide chain, but typically refers to a peptide with a relatively low molecular weight, consisting of about 100 or fewer (preferably 60 or fewer, such as 50 or fewer) total amino acid residues.

Unless otherwise specified, the term "amino acid residue" in this Description encompasses the N-terminal amino acid and C-terminal amino acid of the peptide chain.

In the amino acid sequences described in this Description, the left end is normally the N-end and the right end is normally the C-end.

A "modified amino acid sequence" of a specific amino acid sequence in this Description is an amino acid sequence formed by substituting, deleting and/or adding (inserting) one or several (typically two or three) amino acid residues without detracting from the function (such as the calreticulin expression-promoting activity of the calreticulin expression-promoting peptide) of that specific amino acid sequence. Typical examples of modified amino acid sequences as defined in the Description include sequences produced by so-called conservative amino acid replacement of one or several (typically two or three) amino acid residues (for example, sequences produced by substitution of a basic amino acid residue for another basic amino acid residue, such as mutual substitution of a lysine residue and an arginine residue), and sequences produced by addition (insertion) or deletion of one or several (typically two or three) amino acid residues in a specific amino acid sequence. Thus, the calreticulin expression-promoting peptide disclosed here includes not only synthetic peptides having amino acid sequences identical to those of the sequence numbers, but also synthetic peptides having amino acid sequences comprising the amino acid sequences of the sequence numbers with one or several (typically two or three) amino acid residues substituted (by the above conservative amino acid replacement, for example), deleted and/or added therein, and having equivalent calreticulin expression-promoting activity.

In this Description, a "stem cell" is a cell having self-replicating ability, and capable of differentiating into one or more or preferably two or more kinds of cells, tissues, or organs. In this Description, stem cells are embryonic stem (ES) cells, iPS cells, embryonic germ (EG) cells and somatic stem cells (also called tissue stem cells). Examples include neural stem cells, hematopoietic stem cells, mesenchymal stem cells, hepatic stem cells, dermal stem cells, germ stem cells, muscle stem cells and the like, but are not limited to these as long as they have the aforementioned abilities.

In this Description, a "pluripotent stem cell" is a stem cell having the potential to differentiate into various kinds of cells forming a living body (excluding placenta and other extraembryonic tissue), and having self-replicating ability in an undifferentiated state. In this Description, a pluripotent stem cell may be an ES cell, iPS cell or EG cell, but is not limited to these as long as it has the aforementioned abilities.

In this Description, the term "tumor" is defined in the broad sense to encompass tumors in general (typically malignant tumors), including carcinomas, sarcomas, and lesions of the blood and hematopoietic tissue (leukemia, lymphomas, etc.). A "tumor cell" is a cell forming such a tumor, and is typically a cell that has begun to proliferate abnormally irrespective of the surrounding normal tissue (that is, a cancerous cell). Thus, unless otherwise specified, any cell that is classified as a tumor cell (cancer cell) rather than a normal cell is called a tumor cell regardless of its origin or properties. The cells making up epithelial tumors (squamous epithelial cancer, adenocarcinoma, etc.), non-epithelial tumors (various sarcomas, bone cancer, etc.), various cytomas (neuroblastoma, retinoblastoma, etc.), and lymphoma, melanoma and the like are included here as tumor cells.

In this Description, the terms "genomically stable" or "genomically unstable" are defined in a broad sense to describe the conditions of cells classified (evaluated) on the basis of the presence or absence or degree of structural and/or functional abnormalities of the genome. Examples of structural and/or functional abnormalities of the genome include the presence or absence or degree of chromosomal abnormalities (for example, the partial chromosomal abnormalities of partial duplication, inversion, deletion, translocation and breakage, as well as aploids (chromosomal numerical aberrations), multinuclearity and the like). Chromosomal abnormalities here may also encompass so-called "karyotypic abnormalities". Of the chromosomal abnormalities, the presence or absence or degree of aploids (preferably duplication anomalies) can be used favorably as a basis for evaluation in the present invention. However, these chromosomal abnormalities are examples of such bases for evaluation, and are not intended to restrict the present invention.

The calreticulin expression-promoting peptide disclosed here is a synthetic peptide having a calreticulin expression-promoting peptide sequence that was discovered by the inventors to have the potential to increase the expressed amount of calreticulin (preferably, the amount of calreticulin present on the cell surfaces (typically, cell membrane surfaces)) or to promote calreticulin expression (that is, calreticulin expression-promoting activity) in target eukaryotic cells when supplied to such cells (typically, to medium in which such cells are cultured). Examples of calreticulin expression-promoting peptide sequences that can be used favorably in implementing the present invention are listed under SEQ ID NOs: 6 to 74. Specifically, these are as follows.

The amino acids of SEQ ID NOs: 6 to 44 are siRNA-associated sequences of spindle formation-associated proteins.

Specifically, the amino acid sequences of SEQ ID NOs: 6 and 7 are siRNA-associated sequences of the human centrin 2 protein, each corresponding to an amino acid sequence comprising a total of 9 amino acid residues. Centrins are centrosome-associated proteins that occur in the centrosome of eukaryotic organisms, are involved in centriole replication and microtubule breakage as constituent proteins of the centriole, and play an important role in spindle formation. Centrin 2 is a protein in the centrin family (typically, centrin 1, centrin 2, centrin 3, etc.).

The amino acid sequence of SEQ ID NO: 8 consists of a total of 8 amino acid residues, and is an siRNA-associated sequence of a protein called Cytoskeleton-associated protein 5 (CKAP5) or Colonic and hepatic tumor overexpressed gene protein (CH-TOG). The CKAP5 protein binds to the plus ends of microtubules, and controls microtubule kinetics, microtubule formation and the like. This protein promotes nucleus formation and elongation of cytoplasmic microtubules, and plays an important role in spindle formation.

The amino acid sequence of SEQ ID NO: 9 corresponds to an amino acid sequence comprising a total of 8 amino acids that is an siRNA-associated sequence of CKAP5.

The amino acid sequence of SEQ ID NO: 10 corresponds to an amino acid sequence comprising a total of 6 amino acid residues that is an siRNA-associated sequence of CKAP5.

The amino acid sequence of SEQ ID NO: 11 corresponds to an amino acid sequence comprising a total of 9 amino acid residues that is an siRNA-associated sequence of CKAP5.

The amino acid sequence of SEQ ID NO: 12 corresponds to an amino acid sequence comprising a total of 6 amino acid residues that is an siRNA-associated sequence of CKAP5.

The amino acid sequence of SEQ ID NO: 13 corresponds to an amino acid sequence comprising a total of 5 amino acid residues that is an siRNA-associated sequence of CKAP5.

The amino acid sequence of SEQ ID NO: 14 corresponds to an amino acid sequence comprising a total of 6 amino acid residues that is an siRNA-associated sequence of CKAP5.

The amino acid sequence of SEQ ID NO: 15 corresponds to an amino acid sequence comprising a total of 8 amino acid residues that is an siRNA-associated sequence of Centrosomal protein of 164 kDa (CEP164). CEP164 is a protein involved in microtubule formation and maintaining the structure of primary cilia and the like, and plays an important role in spindle formation. This protein also plays an important role in the G2/M checkpoint, nuclear division and chromosome segregation.

The amino acid sequence of SEQ ID NO: 16 corresponds to an amino acid sequence comprising a total of 6 amino acid residues that is an siRNA-associated sequence of CEP 164.

The amino acid sequence of SEQ ID NO: 17 corresponds to an amino acid sequence comprising a total of 6 amino acid residues that is an siRNA-associated sequence of CEP 164.

The amino acid sequence of SEQ ID NO: 18 corresponds to an amino acid sequence comprising a total of 5 amino acid residues that is an siRNA-associated sequence of CEP 164.

The amino acid sequence of SEQ ID NO: 19 corresponds to an amino acid sequence comprising a total of 8 amino acid residues that is an siRNA-associated sequence of kinetochore protein NDC80 (also called NDC80). NDC80 is a protein involved in kinetochore integrity and the organization of stable microtubule binding sites in the outer plate of the kinetochore, and plays an important role in spindle formation.

The amino acid sequence of SEQ ID NO: 20 corresponds to an amino acid sequence comprising a total of 5 amino acid residues that is an siRNA-associated sequence of NDC80.

The amino acid sequence of SEQ ID NO: 21 corresponds to an amino acid sequence comprising a total of 6 amino acid residues that is an siRNA-associated sequence of NDC80.

The amino acid sequence of SEQ ID NO: 22 corresponds to an amino acid sequence comprising a total of 5 amino acid residues that is an siRNA-associated sequence of NDC80.

The amino acid sequence of SEQ ID NO: 23 corresponds to an amino acid sequence comprising a total of 8 amino acid residues that is an siRNA-associated sequence of Cell division control protein 48 (CDC48). CDC48 is a protein involved in spindle disassembly, degradation of ubiquitinated proteins and the like, and plays an important role in spindle formation.

The amino acid sequence of SEQ ID NO: 24 corresponds to an amino acid sequence comprising a total of 7 amino acid residues that is an siRNA-associated sequence of the Inner centromere protein (INCENP). INCENP is a constituent protein of the chromosomal passenger complex (CPC), and plays an important role in microtubule stabilization, spindle assembly and the like.

The amino acid sequence of SEQ ID NO: 25 corresponds to an amino acid sequence comprising a total of 6 amino acid residues that is an siRNA-associated sequence of INCENP.

The amino acid sequence of SEQ ID NO: 26 corresponds to an amino acid sequence comprising a total of 5 amino acid residues that is an siRNA-associated sequence of INCENP.

The amino acid sequence of SEQ ID NO: 27 corresponds to an amino acid sequence comprising a total of 6 amino acid residues that is an siRNA-associated sequence of INCENP.

The amino acid sequence of SEQ ID NO: 28 corresponds to an amino acid sequence comprising a total of 8 amino acid residues that is an siRNA-associated sequence of Survivin (sometimes called Baculoviral IAP repeat containing protein 5 (BIRC5)), an inhibition of apoptosis family protein (IAP family protein). BRIC5 is a constituent protein of the chromosomal passenger complex (CPC), and plays an important role in microtubule stabilization, spindle assembly and the like.

The amino acid sequence of SEQ ID NO: 29 corresponds to an amino acid sequence comprising a total of 7 amino acid residues that is an siRNA-associated sequence of BIRC5.

The amino acid sequence of SEQ ID NO: 30 corresponds to an amino acid sequence comprising a total of 7 amino acid residues that is an siRNA-associated sequence of BIRC5.

The amino acid sequence of SEQ ID NO: 31 corresponds to an amino acid sequence comprising a total of 6 amino acid residues that is an siRNA-associated sequence of BIRC5.

The amino acid sequence of SEQ ID NO: 32 corresponds to an amino acid sequence consisting of a total of 6 amino acid residues that is an siRNA-associated sequence of BIRC5.

The amino acid sequence of SEQ ID NO: 33 corresponds to an amino acid sequence comprising a total of 5 amino acid residues that is an siRNA-associated sequence of BIRC5.

The amino acid sequence of SEQ ID NO: 34 corresponds to an amino acid sequence comprising a total of 9 amino acid residues that is an siRNA-associated sequence of Microtubeassociated protein 215 (MAP215). MAP215 is one of a group of proteins (microtubule-associated proteins; MAP) that bind to microtubules (specifically to tubulin). It is involved in microtubule stabilization, microtubule polymerization and the like, and plays an important role in spindle formation.

The amino acid sequence of SEQ ID NO: 35 corresponds to an amino acid sequence comprising a total of 9 amino acid residues that is an siRNA-associated sequence of MAP215.

The amino acid sequence of SEQ ID NO: 36 corresponds to an amino acid sequence comprising a total of 9 amino acid residues that is an siRNA-associated sequence of MAP215.

The amino acid sequence of SEQ ID NO: 37 corresponds to an amino acid sequence comprising a total of 7 amino acid residues that is an siRNA-associated sequence of the kinesin-associated motor protein EG5. EG5 is a protein associated with bipolar spindle formation and the like, and plays an important role in spindle formation.

The amino acid sequence of SEQ ID NO: 38 corresponds to an amino acid sequence comprising a total of 8 amino acid residues that is an siRNA-associated sequence of EG5.

The amino acid sequence of SEQ ID NO: 39 corresponds to an amino acid sequence comprising a total of 7 amino acid residues that is an siRNA-associated sequence of EG5.

The amino acid sequence of SEQ ID NO: 40 corresponds to an amino acid sequence comprising a total of 8 amino acid residues that is an siRNA-associated sequence of EG5.

The amino acid sequence of SEQ ID NO: 41 corresponds to an amino acid sequence comprising a total of 7 amino acid residues that is an siRNA-associated sequence of EG5.

The amino acid sequence of SEQ ID NO: 42 corresponds to an amino acid sequence comprising a total of 6 amino acid residues that is an siRNA-associated sequence of Cell division cycle-associated protein 8 (CDCA8). CDCA8 is a constituent protein of the chromosomal passenger complex (CPC), and plays an important role in microtubule stabilization, spindle assembly and the like.

The amino acid sequence of SEQ ID NO: 43 corresponds to an amino acid sequence comprising a total of 5 amino acid residues that is an siRNA-associated sequence of CDCA8.

The amino acid sequence of SEQ ID NO: 44 corresponds to an amino acid sequence comprising a total of 6 amino acid residues that is an siRNA-associated sequence of CDCA8.

The amino acid sequences of SEQ ID NOs: 45 to 66 are amino acid sequences of peptides capable of functioning as FtsZ inhibitors or FtsA inhibitors.

Specifically, the amino acid sequences of SEQ ID NOs: 45 to 54 correspond to amino acid sequences comprising a total of 12 amino acid residues that function as FtsZ inhibitors or FtsA inhibitors.

The amino acid sequences of SEQ ID NOs: 55 to 66 correspond to amino acid sequences comprising a total of 9 amino acid residues that function as FtsZ inhibitors or FtsA inhibitors.

The amino acids represented by SEQ ID NOs: 67 to 72 are partial amino acid sequences of cell division proteins (typically, sequences containing partial amino acid sequences of microtubule binding regions of tau proteins).

Specifically, the amino acid sequence of SEQ ID NO: 67 corresponds to an amino acid sequence comprising a total of 15 amino acid residues that is a partial amino acid sequence of a tau protein.

The amino acid sequence of SEQ ID NO: 68 corresponds to an amino acid sequence comprising a total of 7 amino acid residues that is a partial amino acid sequence of a tau protein.

The amino acid sequence of SEQ ID NO: 69 corresponds to an amino acid sequence comprising a total of 17 amino acid residues that is a partial amino acid sequence of a tau protein.

The amino acid sequence of SEQ ID NO: 70 corresponds to an amino acid sequence comprising a total of 11 amino acid residues that is a partial amino acid sequence of a tau protein.

The amino acid sequence of SEQ ID NO: 71 corresponds to an amino acid sequence comprising a total of 11 amino acid residues that is a partial amino acid sequence of a tau protein.

The amino acid sequence of SEQ ID NO:72 corresponds to an amino acid sequence comprising a total of 6 amino acid residues that is a partial amino acid sequence of a tau protein.

The amino acid sequences of SEQ ID NOs: 73 and 74 are amino acid sequences constituting APP signal peptides.

Specifically, the amino acid sequence of SEQ ID NO: 73 corresponds to an amino acid sequence consisting of a total of 17 amino acid residues constituting a mouse APP signal peptide.

The amino acid sequence of SEQ ID NO: 74 corresponds to an amino acid sequence consisting of a total of 17 amino acid residues constituting a human APP signal peptide.

The calreticulin expression-promoting peptide disclosed here may be a synthetic peptide consisting solely of a calreticulin expression-promoting peptide sequence of any of SEQ ID NOs: 6 to 74 or a modified amino acid sequence thereof, but from the standpoint of improving calreticulin expression-promoting activity, it is preferably a synthetic peptide having a transmembrane peptide sequence at the N-end or C-end of such a calreticulin expression-promoting peptide sequence. A synthetic peptide having a transmembrane peptide sequence can improve calreticulin expression-promoting activity because it can be rapidly introduced into a cell when supplied to a target cell.

Any amino acid sequence constituting a transmembrane peptide capable of passing through the cell membrane and/or nuclear membrane can be used as this transmembrane peptide sequence, without any particular limitations. Many desirable transmembrane peptide sequences are known, but for example an amino acid sequence (or modified amino acid sequence) associated with a NoLS (nucleolar localization signal) is desirable as the amino acid sequence of a transmembrane peptide sequence of the calreticulin expression-promoting peptide. Examples include the NoLS amino acid sequence represented by SEQ ID NO: 1, which is contained in LIM kinase 2, and the NoLS amino acid sequence represented by SEQ ID NO: 2, which is contained in IBV (avian infectious bronchitis virus) N protein (nucleocapside protein). Other examples of transmembrane peptide sequences include the amino acid sequences represented by SEQ ID NOs: 3 to 5, and modified amino acid sequences of these (but only those retaining transmembrane properties). SEQ ID NO: 3 represents the amino acid sequence of a transmembrane peptide sequence contained in the TAT protein of HIV (human immunodeficiency virus). SEQ ID NO: 4 represents the amino acid sequence of a transmembrane peptide sequence (PTD4) obtained of a modified form of this TAT. SEQ ID NO: 5 represents an ANT-related amino acid sequence of Antennapedia, a mutant form of *Drosophila*.

The transmembrane peptide sequences described in the sequence tables are only examples, and usable peptide sequences are not limited to these. Various transmembrane sequences that can be used in implementing the present invention are described in various documents already published at the time of this application. The amino acid sequences of these transmembrane peptide sequences can be easily discovered by ordinary search techniques.

The amino acid sequence of SEQ ID NO: 1 (or a modified amino acid sequence thereof), which is also described in Patent Literature 1, is desirable as a transmembrane peptide sequence. Synthetic peptides exhibiting strong calreticulin expression-promoting activity can be obtained by combining the transmembrane peptide sequence described by SEQ ID NO: 1 with the aforementioned calreticulin expression-promoting peptide sequences (SEQ ID NOs: 6 to 74), or modified sequences thereof.

Some of the peptide chains (amino acid sequences) of the calreticulin expression-promoting peptide disclosed here can be constructed by appropriately combining calreticulin expression-promoting peptide sequences such as those described above with transmembrane peptide sequences. Either the calreticulin expression-promoting peptide sequence or the transmembrane peptide sequence can be located at the relative C-end (or N-end). The calreticulin expression-promoting peptide sequence and transmembrane peptide sequence are preferably disposed adjacent to one another. That is, the number of amino acid residues between the calreticulin expression-promoting peptide sequence and the transmembrane peptide sequence that are not included in either sequence part is preferably zero, or if not zero, is preferably about 1 to 3 residues. For example, one or several (typically two or three) amino acid residues (such as one or several glycine (G) residues) may be included as linkers between the calreticulin expression-promoting peptide sequence and the transmembrane peptide sequence.

At least one amino acid residue may be amidated in the calreticulin expression-promoting peptide disclosed here. The structural stability (for example, protease resistance) of the synthetic peptide can be improved by amidating a carboxyl group of an amino acid residue (typically, the C-terminal amino acid residue of the peptide chain).

The calreticulin expression-promoting peptide may contain another sequence (amino acid residue) part in addition to the amino acid sequences constituting the calreticulin expression-promoting peptide sequence and transmembrane peptide sequence as long as the calreticulin expression-promoting activity is not adversely affected. Although this is not a limitation, a sequence capable of maintaining the three-dimensional shape (typically, linear shape) of the calreticulin expression-promoting peptide sequence and transmembrane peptide sequence part is desirable as such a sequence part. The total number of amino acid residues constituting the peptide chain of the calreticulin expression-promoting peptide is suitably 100 or fewer, or preferably 60 or fewer, or more preferably 50 or fewer. For example, a synthetic peptide of 30 or fewer residues is particularly desirable.

Such a short-chain peptide is easy to chemically synthesize, allowing the calreticulin expression-promoting peptide to be provided easily. The conformation (steric structure) of the peptide is not particularly limited as long as calreticulin expression-promoting activity is obtained in the environment of use (in vitro or in vivo), but a linear or helix structure is desirable from the standpoint of avoiding immunogenicity (antigenicity). Peptides of this sort are unlikely to form epitopes. From this perspective, a linear peptide with a relatively low molecular weight (typically 60 or fewer, or preferably 50 or fewer or more preferably 30 or fewer amino acid residues) is preferred as the calreticulin expression-promoting peptide in the present invention.

The proportion of the calreticulin expression-promoting peptide sequence and transmembrane peptide sequence as a percentage of the total amino acid sequence (that is, the number of amino acid residues constituting the calreticulin expression-promoting peptide sequence and transmembrane peptide sequence as a percentage of the total amino acid residues constituting the peptide chain) is not particularly limited as long as the calreticulin expression-promoting activity is not adversely affected, but is preferably about 60% or more, or more preferably 80% or more. At least 90% is especially desirable. A desirable embodiment is a peptide consisting entirely of the calreticulin expression-promoting peptide sequence and the transmembrane peptide sequence (that is, in which these sequences constitute 100% of the total amino acid sequence).

Preferably all the amino acid residues are L-amino acids in the calreticulin expression-promoting peptide of the invention, but D-amino acids may be substituted for some or all of the amino acid residues to the extent that this does not detract from the calreticulin expression-promoting activity.

The calreticulin expression-promoting peptide disclosed here can be easily manufactured by ordinary chemical synthesis methods. For example, either conventional known solid-phase synthesis methods or liquid-phase synthesis methods may be adopted. Solid-phase synthesis using Boc (t-butyloxycarbonyl) or Fmoc (9-fluorenylmethoxycarbonyl) amino protecting groups is desirable.

For the calreticulin expression-promoting peptide disclosed here, a peptide chain having the desired amino acid sequence and modifications (C-terminal amidation, etc.) can be synthesized by solid-phase synthesis using a commercial peptide synthesizer (available from Intavis AG or Protein Technologies for example).

The calreticulin expression-promoting peptide may also be biosynthesized based on genetic engineering techniques. That is, a polynucleotide (typically DNA) is synthesized with a nucleotide sequence (including ATG initiation codon) coding for the amino acid sequence of the desired calreticulin expression-promoting peptide. A recombinant vector containing a gene expression construct comprising the synthesized polynucleotide (DNA) together with various regulatory elements (including promoters, ribosome-binding sites, terminators, enhancers, and various cis-elements for controlling expression level) necessary for expressing the amino acid sequence in host cells is then constructed according to the host cells.

This recombinant vector is then introduced into specific host cells (such as yeast cells, insect cells or plant cells) by ordinary methods, and the host cells or a tissue or organism containing the host cells is then cultured under specific conditions. The target peptide can thus be expressed and produced in the cells. The peptide can then be isolated from the host cells (or the medium if secreted), and refolded and purified as necessary to obtain the target calreticulin expression-promoting peptide.

Methods conventionally used in the field may be adopted as is for constructing the recombinant vector, introducing the constructed recombinant vector into host cells and the like, and these methods are not explained in detail because they are not a feature of the invention.

For example, a fusion protein expression system can be used to achieve efficient large-scale production in host cells. That is, a gene (DNA) coding for the amino acid sequence of the target calreticulin expression-promoting peptide is chemically synthesized, and introduced into a suitable site of a suitable fusion protein expression vector (for example, a GST (Glutathione S-transferase) fusion protein expression vector such as the pET series from Novagen or the pGEX series from Amerscham Biosciences). The host cells (typically E. coli) are then transformed with this vector. The resulting transformant is cultured to prepare the target fusion protein. Next, the protein is extracted and purified. The resulting purified fusion protein is then cleaved with a specific enzyme (protease), and the released target peptide fragment (designed calreticulin expression-promoting peptide) are collected by a method such as affinity chromatography. These are then refolded as necessary by suitable methods. The calreticulin expression-promoting peptide disclosed here may be manufactured using such a conventional known fusion protein expression system (using a GST/His system from Amersham Biosciences for example).

Alternatively, template DNA for a cell-free protein synthesis system (that is, a synthetic gene fragment containing a nucleotide sequence coding for the amino acid sequence of the calreticulin expression-promoting peptide) can be constructed, and the target polypeptide can be synthesized in vitro by a cell-free protein synthesis system using various chemicals necessary for peptide synthesis (ATP, RNA polymerase, amino acids, etc.). The literature of Shimizu et al (Shimizu et al., Nature Biotechnology, 19, 751-755 (2001)) and Madin et al (Madin et al., Proc. Natl. Acad. Sci. USA, 97(2), 559-564 (2000)) can be consulted regarding cell-free protein synthesis systems. At the time of this application many enterprises are already engaged in contract production of polypeptides based on the techniques described in this literature, and cell-free protein synthesis kits (such as a Wheat germ cell-free protein synthesis kit available from CellFree Sciences in Japan) are commercially available.

A nucleotide sequence coding for the calreticulin expression-promoting peptide disclosed here and/or a single- or double-stranded polynucleotide containing a nucleotide sequence complementary to this sequence can be easily manufactured (synthesized) by conventional known methods. That is, a nucleotide sequence corresponding to the amino acid sequence of the calreticulin expression-promoting peptide is determined and provided by selecting codons corresponding to the individual amino acid residues constituting the designed amino acid sequence. Once the nucleotide sequence has been determined, a (single-stranded) polynucleotide corresponding to the desired nucleotide sequence can be easily obtained with a DNA synthesizer or the like. The resulting single-stranded DNA can then be used as a template to obtain target double-stranded DNA using various enzymatic synthesis techniques (typically PCR). The polynucleotide may also be in the form of RNA (mRNA or the like) rather than DNA. DNA may be provided as double-stranded or single-stranded DNA. When single-stranded it may be either a coding strand (sense strand) or a non-coding strand (antisense strand) having a sequence complementary to the coding strand.

As discussed above, the resulting polynucleotide can be used as a material in the construction of a recombinant gene (expression cassette) for producing the calreticulin expression-promoting peptide in various host cells or with a cell-free protein synthesis system.

The calreticulin expression-promoting peptide disclosed here may also be in the form of a salt as long as the calreticulin expression-promoting activity is not diminished in the target cells. For example, it is possible to use an acid-addition salt of the peptide, which can be obtained by ordinary methods by an addition reaction with a commonly used inorganic acid or organic acid. Another salt (such as a metal salt) is also possible as long as the calreticulin expression-promoting activity is retained in the target cells. Consequently, the "peptide" described in this Description and in the Claims encompasses such salt forms.

The calreticulin expression promoter disclosed here may contain various carriers according to the mode of use as long as the active ingredient (calreticulin expression-promoting peptide) is retained without any loss of its calreticulin expression-promoting ability. Carriers commonly used in peptide drugs are preferred as diluents, excipients and the like. These may differ according to the use and form of the calreticulin expression promoter, but typical examples include water, physiological buffer, and various organic solvents. Aqueous alcohol (such as ethanol) solutions of suitable concentrations, glycerol, and olive oil and other non-drying oils are also possible, as are liposomes. Examples of accessory ingredients that may be included in the calreticulin expression promoter include various fillers, extenders, binders, humectants, surfactants, pigments, perfumes and the like.

The form of the calreticulin expression promoter is not particularly limited. For example, typical forms include liquids, suspensions, emulsions, aerosols, foams, granules, powders, tablets, capsules, ointments, aqueous gels and the like. It may also be in the form of a freeze-dried preparation or granules to be dissolved in saline or a suitable buffer (such as phosphate-buffered saline (PBS)) immediately before use to prepare a liquid.

The actual processes for preparing various forms of drugs (compositions) using the calreticulin expression-promoting peptide (primary ingredient) and various carriers (secondary ingredients) as materials may conform to conventional known methods, and these formulation methods are not explained in detail because they are not a feature of the invention. Detailed information about formulation is given in Comprehensive Medicinal Chemistry, Corwin Hansch Ed., Pergamon Press (1990) for example. The entire content of this book is incorporated by reference in this Description.

There are no particular limits on the cells to which the calreticulin expression promoter (that is, the calreticulin expression-promoting peptide) disclosed here is applied, and calreticulin expression can be promoted in the cells of various organisms (limited however to eukaryotes). Examples include somatic cells (such as neural cells, myocardial cells, dermal cells, germ cells, vascular endothelial cells, hepatic cells, pancreatic cells, etc.), tumor cells, stem cells (including ES cells, iPS cells, EG cells, and somatic stem cells) and the like from humans and other animals (typically vertebrates, especially mammals). Tumor cells, stem cells and neural cells (for example, neurons, astrocytes and oligodendrocytes) are particularly desirable for use with the calreticulin expression promoter (that is, the calreticulin expression-promoting peptide) disclosed here.

The calreticulin expression promoter (that is, calreticulin expression-promoting peptide) disclosed here can be used by a method and in a dosage suited to the object and form of the promoter.

In the case of cells (typically cultured cells) cultured (passaged) in vitro, for example, a suitable amount of the calreticulin expression promoter (calreticulin expression-promoting peptide) disclosed here can be added to medium at any stage of the culture process (preferably at the beginning of culture, or at an early stage after beginning of culture). The added amount and number of additions are not particularly limited, and may differ depending on the type and condition of the target cells and on the cell density (cell density at beginning of culture), number of passages, culture conditions, medium type and other conditions. Typically, the promoter is added one to multiple times (for example, at beginning of culture and then additionally during each passage and medium replacement) so as to achieve a peptide concentration in the medium in the range of about 0.1 µM to 100 µM, or preferably 0.1 µM to 50 µM, or more preferably 0.5 µM to 20 µM (such as 1 µM to 10 µM).

Alternatively, the desired amount of the calreticulin expression promoter (calreticulin expression-promoting peptide) disclosed here may be supplied (administered) to a living body (that is, a patient) as a liquid, as a pill or other solid form or as an ointment or other gel or aqueous jelly. Examples of administration methods include intravenous administration, injection into target tissue or the like, and oral administration. It is thus possible to promote calreticulin expression in target cells, and especially in genomically unstable cells. Thus, the calreticulin expression promoter (calreticulin expression-promoting peptide) may be used for example as a composition for removing genomically unstable cells based on the immune response of the subject receiving the calreticulin expression promoter, or for detecting (screening) genomically unstable cells in vivo.

In the calreticulin expression-promoting method disclosed here, a culture of target eukaryotic cells is prepared, the calreticulin expression-promoting peptide (that is, a calreticulin expression promoter containing this synthetic peptide as an active ingredient) is supplied at least once to the culture of the target cells (typically, to the medium of the cell culture), and the cell culture to which the synthetic peptide has been supplied at least once is cultured for a specified amount of time. A cell culture containing calreticulin high-expression cells can be manufactured by this method.

There are no particular limits on the cells targeted by the calreticulin expression-promoting method disclosed here (or by a method for manufacturing calreticulin high-expression cells encompassing this method), and calreticulin expression can be promoted in cells derived from various organisms (limited however to eukaryotes). Examples include somatic cells (for example, neural cells, cardiac muscle cells, dermal cells, germ cells, vascular endothelial cells, hepatic cells, pancreatic cells, etc.), tumor cells, and stem cells (including ES cells, iPS cells, EG cells and somatic stem cells) from humans and other animals (typically, vertebrates, especially mammals). Tumor cells, stem cells and neural cells (for example, neurons, astrocytes and oligodendrocytes) are particularly desirable as targets of the calreticulin expression promoter (calreticulin expression-promoting peptide) disclosed here.

The cells in the cell culture disclosed here are not particularly limited as long as they are cells targeted by the calreticulin expression promoting method described above, and may be various kinds of cultured cells including initial culture cells, passage cells and cell lines. The cells in the culture may also be cells that have undergone molecular biological manipulation. For example, they may be cells having a telomerase (TERT) gene introduced for purposes of establishing a cell line or the like.

No special processes are involved in the method of supplying the calreticulin expression-promoting peptide (calreticulin expression promoter) disclosed here to the cultured cells. For example, this may be accomplished by adding a suitable amount of the calreticulin expression-promoting peptide (or a composition containing this peptide as an active ingredient) to a culture (typically a culture liquid) in which the target cells are being cultured.

The time taken for culture after addition of the calreticulin expression-promoting peptide to the culture of the target cells (typically, to the medium of the cell culture) may be any time sufficient to allow promotion of calreticulin expression or to increase the expressed amount of calreticulin in the target cells, without any particular limitations. Typically, culture is continued for a few hours to a few days. For example, culture may be performed for 2 hours or more, or preferably 24 hours or more, or more preferably 48 hours or more, and for example culture may performed for 3 to 5 days, or 6 to 7 days, or about 10 days from the beginning of culture.

Some examples of the present invention are explained below, but the intent is not to limit the present invention to what is shown in these examples.

EXAMPLES

Example 1: Peptide Synthesis

A total of 12 kinds of peptides (Samples 1 to 12) were manufactured using the peptide synthesizer described below. Table 1 lists the amino acid sequences and the like of these synthetic peptides.

TABLE 1

| Sample No. | Amino acid sequence | Total amino acid residues |
|---|---|---|
| 1 | CRAKAGDPC (SEQ ID NO: 6) | 9 |
| 2 | CGNSCSHC (SEQ ID NO: 8) | 8 |
| 3 | NPGASF (SEQ ID NO: 17) | 6 |
| 4 | CQRKPTIC (SEQ ID NO: 28) | 8 |
| 5 | GPRPPSLEC (SEQ ID NO: 63) | 9 |
| 6 | VQIINKK (SEQ ID NO: 68) | 7 |
| 7 | IGSLDNITHVPGGGNKK (SEQ ID NO: 69) | 17 |
| 8 | MLPSLALLLLAAWTVRA (SEQ ID NO: 73) | 17 |
| 9 | KKRTLRKNDRKKR CRAKAGDPC (SEQ ID NO: 75) | 22 |
| 10 | KKRTLRKNDRKKR NPGASF (SEQ ID NO: 76) | 19 |
| 11 | KKRTLRKNDRKKR GPRPPSLEC (SEQ ID NO: 77) | 22 |
| 12 | LAARAVRFSEKV (SEQ ID NO: 78) | 12 |

As shown in Table 1, each of the peptides of Samples 1 to 8 is a synthetic peptide comprising a calreticulin expression-promoting peptide sequence represented by the corresponding sequence ID number in the table.

Specifically, the peptides of Samples 1 to 4 are synthetic peptides comprising siRNA-associated sequences of spindle formation-association proteins. That is, the peptide of Sample 1 is a synthetic peptide comprising the Centrin 2 protein siRNA-associated sequence of SEQ ID NO: 6, the peptide of Sample 2 comprises the CKAP5C siRNA-associated sequence of SEQ ID NO: 8, the peptide of Sample 3 comprises the CEP164 siRNA-associated sequence of SEQ ID NO: 17, and the peptide of Sample 4 comprises the BRIC5 siRNA-associated sequence of SEQ ID NO: 28.

The peptide of Sample 5 is a synthetic peptide comprising the amino acid sequence represented by SEQ ID NO: 63, which functions as an FtsZ inhibitor or FtsA inhibitor.

The peptides of Samples 6 and 7 are synthetic peptides comprising partial amino acid sequences of cell division proteins. That is, the peptides of Samples 6 and 7 are synthetic peptides comprising the sequences of SEQ ID NOs: 68 and 69, which are partial amino acid sequences of tau proteins.

The peptide of Sample 8 is a synthetic peptide comprising the amino acid sequence of SEQ ID NO: 73, which constitutes a mouse-derived APP signal peptide.

Also, as shown in Table 1, each of the peptides of Samples 9 to 11 is a synthetic peptide constructed by combining a calreticulin expression-promoting peptide sequence with a transmembrane peptide sequence.

Specifically, the peptide of Sample 9 is a synthetic peptide (SEQ ID NO: 75) having the calreticulin expression-promoting peptide sequence of SEQ ID NO: 6 at the C-end of the peptide chain and an amino acid sequence (SEQ ID NO: 1) from LIM kinase 2 as a transmembrane peptide sequence at the N-end.

The peptide of Sample 10 is a synthetic peptide (SEQ ID NO: 76) having the calreticulin expression-promoting peptide sequence of SEQ ID NO: 17 at the C-end of the peptide chain and an amino acid sequence (SEQ ID NO: 1) from LIM kinase 2 as a transmembrane peptide sequence at the N-end.

The peptide of Sample 11 is a synthetic peptide (SEQ ID NO: 77) having the calreticulin expression-promoting peptide sequence of SEQ ID NO: 63 at the C-end of the peptide chain and an amino acid sequence (SEQ ID NO: 1) from LIM kinase 2 as a transmembrane peptide sequence at the N-end.

The peptide of Sample 12 is a synthetic peptide (SEQ ID NO: 78) constructed by combining 12 random amino acid residues as a comparative example of a calreticulin expression-promoting peptide.

The synthetic peptides above are linear peptides, and were synthesized by solid-phase synthesis (Fmoc method) using a commercial peptide synthesizer (made by Intavis AG) according to the manual. The mode of use of the peptide synthesizer is not explained in detailed because it is not a feature of the invention.

The peptides of the synthesized Samples 1 to 12 were dissolved in PBS (−) or DMSO to prepare peptide stock solutions.

Example 2: Evaluation of Calreticulin Expression-Promoting Activity of Synthetic Peptides in Tumor Cells The calreticulin expression-promoting activity of the peptides of the Samples 1 to 12 obtained in Example 1 above was investigated. The sample cells were HeLaS3 cells (ATCC CCL2.2), a cultured cell line derived from human cervical cancer. These HeLaS3 cells (ATCC CCL2.2) are known as a genomically unstable cultured cell line, which has been confirmed to have multiple chromosome duplications or in other words chromosomal abnormalities (karyotypic abnormalities). The details of the evaluation test are as follows.

HeLaS3 cells were seeded on 8-well slides to a cell density of about $1\times10^3$ cells per well. Using ordinary DMEM medium (Wako Pure Chemical, Cat. No. 043-30085) containing 10% FBS, 100 unit/mL penicillin and 100 μg/mL streptomycin as the medium, the cells were cultured overnight in an incubator under conditions of 5% $CO_2$, 37° C. (the DMEM medium above containing FBS, penicillin and streptomycin is sometimes called DMEM medium below). After this overnight culture, the medium was replaced with DMEM medium containing the peptides of Samples 1 to 12 in an amount yielding a peptide concentration of 10 μM of the medium, and cultured for 5 days. During this 5-day culture period, the medium was replaced every day with DMEM medium containing the peptides of Samples 1 to 12 in an amount yielding a peptide concentration of 10 μM. A peptide-free group was established as a control group.

After completion of this culture, calreticulin expression in each test group was investigated by the following immunofluorescent antibody technique (also called fluorescent immunostaining).

Specifically, the medium was first removed from the culture container of each test group, which was then washed with PBS (−). Cold methanol was then added, and the samples were left for 15 minutes on ice to fix the HeLaS3 cells. The methanol was then removed, PBS (−) containing 3% BSA was added, and the cells were blocked for 1 hour at room temperature. After a specified amount of time, the PBS (−) containing 3% BSA was removed, and the samples were washed with PBS (−).

A diluted primary antibody solution comprising an anti-calreticulin monoclonal [FMC75] antibody (from mouse, Abcam, Cat. No. ab22683, Lot No. GR56669-4) as the primary antibody prepared with 1% BSA/PBS (−) (PBS (−) containing 1% BSA) to a final concentration of $2.5\times10^{-3}$ mg/mL was added to the culture containers of the HeLaS3 cells, and left overnight at 4° C. After the specified elapsed time for this antigen-antibody reaction, the diluted primary antibody solution was removed, followed by washing with PBS (−). A diluted secondary antibody solution consisting of an anti-mouse IgG antibody (goat, Life Technologies, A11001) labeled with a fluorescent dye (Alexa™ 488) and prepared to a final concentration of $10\times10^{-3}$ mg/mL with 1% BSA/PBS (−) was then added as a secondary antibody, and left for 2 hours at room temperature. After the specified amount of time, the diluted secondary antibody solution was removed, and the samples were washed with PBS (−). This was then sealed with a cover glass together with an enclosed liquid containing DAPI (4′,6-diamidino-2-phenylindole) (Life Technologies), and fluorescence was observed by confocal laser microscopy.

The results of fluorescence observation by confocal laser microscopy are shown in FIGS. 1 to 13. These figures are fluorescence micrographs examining calreticulin expression in each test group, and each combines (merges) a fluorescent image showing results for calreticulin expression in HeLaS3 cells as measured by the immunofluorescent antibody technique with an image showing nuclear staining by DAPI. The results for the Sample 1 to Sample 12 groups are shown in FIGS. 1 to 12 with the corresponding numbers, while the results for the peptide-free group are shown in FIG. 13.

Figure 13:
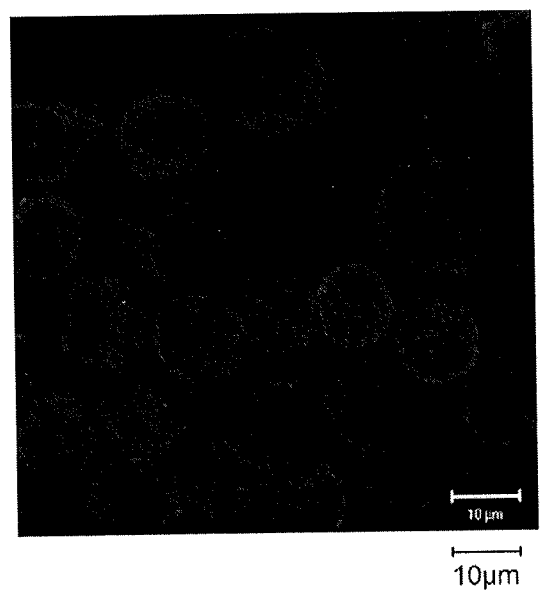
FIG. 13 is a fluorescence micrograph (image) examining the calreticulin expression state of HeLaS3 cells cultured with no peptide added to the HeLaS3 cells.

The results of the evaluation test confirm that with the HeLaS3 cells (FIGS. 1 to 8) treated with the synthetic peptides of Samples 1 to 8 (calreticulin expression-promoting peptides), the fluorescent label indicating calreticulin exhibited stronger fluorescence than in the peptide-free group (FIG. 13). By contrast, with the HeLaS3 cells (FIG. 12) treated with the synthetic peptide of Sample 12 (peptide comprising random amino acid sequence) almost no fluorescence was detected from the fluorescent label as a measure of calreticulin, the same as in the peptide-free group (FIG. 13). That is, the synthetic peptides of Samples 1 to 8 were confirmed to dramatically increase the expressed amount of calreticulin in HeLaS3 cells.

Moreover, comparing the HeLaS3 cells (FIGS. 9 to 11) treated with the synthetic peptides of Samples 9 to 11, which were constructed by combining calreticulin expression-promoting peptide sequences with transmembrane peptide sequences, and the HeLaS3 cells (FIGS. 1, 3, 5) treated with the peptides of Samples 1, 3 and 5, which consisted only of the same calreticulin expression-promoting peptide sequences, it was confirmed that with the HeLaS3 cells of the Sample 9 to 11 groups, the fluorescent labels indicating calreticulin exhibited fluorescence equal to or greater than that seen in the HeLaS3 cells in the Sample 1, 3 and 5 groups. That is, the synthetic peptides of Samples 9 to 11 were confirmed to increase the expressed amount of calreticulin in HeLaS3 cells as much as or more than the synthetic peptides of Samples 1, 3 and 5, respectively.

This shows that the calreticulin expression-promoting peptide disclosed here (that is, a calreticulin expression promoter containing this peptide as an active ingredient) is a peptide (composition) capable of dramatically increasing calreticulin expression in tumor cells (typically HeLa cells). It also shows that a calreticulin expression-promoting peptide having a transmembrane peptide sequence has even stronger calreticulin expression-promoting activity because the transmembrane peptide sequence causes the calreticulin expression-promoting peptide sequence to be introduced more efficiently into cells.

Example 3: Evaluation of Calreticulin Expression-Promoting Activity of Synthetic Peptide in Stem Cells The calreticulin expression-promoting activity of the Samples 1 to 12 obtained in Example 1 was investigated. iPS cells (clone name 201B2, sometimes called simply 201B2 below) established from human fibroblasts were used as the test cells (source: Takahashi K et al., Cell, 131, 861-872 (2007)). These iPS cells were supplied by the Center for iPS Cell Research and Application, Kyoto University.

The test iPS cells (201B2) were seeded to a cell density of about $1 \times 10^4$ cells per well on matrigel-coated 8-well slides. Using mTeSR™ 1 medium (Stemcell Technologies) as the medium, the cells were cultured overnight in an incubator under conditions of 5% $CO_2$, 37° C. Following this overnight culture, fresh mTeSR™ medium containing the peptides of Samples 1 to 12 in an amount yielding a peptide concentration of 10 μM was substituted, and the cells were further cultured for 5 days under the same conditions. Every day during this 5-day culture period, the medium was replaced with mTeSR™ 1 medium containing the peptides of Samples 1 to 12 in an amount yielding a peptide concentration of 10 μM. A peptide-free group was established as a control.

After completion of this culture, calreticulin expression in each test group was investigated by the immunofluorescent antibody technique (fluorescent immunostaining) using an anti-calreticulin antibody as in Example 2 except that a mixed solution of 1 vol. methanol and 1 vol. acetone (methanol:acetone=1:1 solution) was used to fix the cells, and the final concentration of the primary antibody was adjusted to $4 \times 10^{-3}$ mg/mL.

Figure 14:
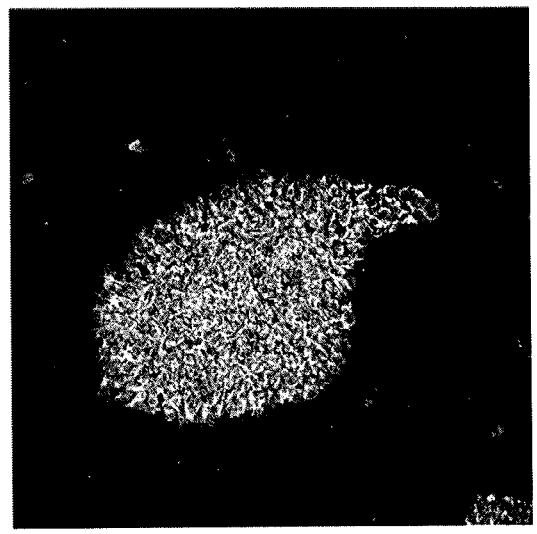
FIG. 14 is a fluorescence micrograph (image) examining the calreticulin expression state of iPS cells (induced pluripotent stem cells) cultured after addition of a calreticulin expression-promoting peptide (Sample 9) of one embodiment to those iPS cells.
Figure 15:
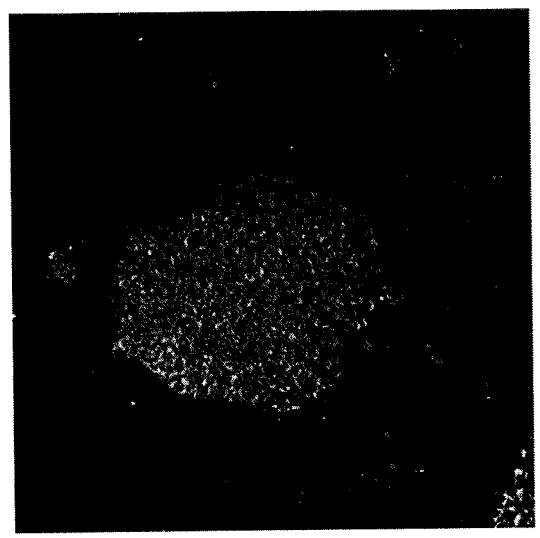
FIG. 15 is a fluorescence micrograph (image) examining the calreticulin expression state of iPS cells cultured with no calreticulin expression-promoting peptide added to the iPS cells.

The results of fluorescence observation by confocal laser microscopy are shown in FIG. 14 and FIG. 15. FIG. 14 shows the results for the Sample 9 group, and FIG. 15 the results for the peptide-free group. These figures are fluorescence micrographs examining calreticulin expression in each test group, and each combines (merges) a fluorescent image showing results for calreticulin expression in iPS cells as measured by the immunofluorescent antibody technique with an image showing nuclear staining by DAPI.

As shown in FIG. 14 and FIG. 15, with the iPS cells (FIG. 14) treated with the synthetic peptide (calreticulin expression-promoting peptide) of Sample 9, the fluorescent label indicating calreticulin exhibited stronger fluorescence than in the case of the iPS cells of the peptide-free group (FIG. 15) and the iPS cells (not shown) treated with the synthetic peptide of Sample 12 (peptide comprising random amino acid sequence). Moreover, although the results are not shown here, strong fluorescence from the fluorescent label indicating calreticulin was also confirmed with the iPS cells treated with the synthetic peptides of Samples 1 to 8 and Samples 10 and 11 (calreticulin expression-promoting peptides). That is, the synthetic peptides of Samples 1 to 11 were confirmed to dramatically increase expressed amounts of calreticulin in iPS cells.

With the synthetic peptides of Samples 9 to 11 having transmembrane peptide sequences, the expressed amount of calreticulin in the iPS cells was confirmed to be equal to or greater than that obtained with the Samples 1, 3 and 5 consisting only of calreticulin expression-promoting peptide sequences.

This shows that the calreticulin expression-promoting peptide disclosed here (that is, a calreticulin expression promoter containing this peptide as an active ingredient) is a peptide (composition) capable of dramatically increasing calreticulin expression in stem cells (typically human iPS cells). It also shows that a calreticulin expression-promoting peptide having a transmembrane peptide sequence exhibits even stronger calreticulin expression-promoting activity because the transmembrane peptide sequence causes the calreticulin expression-promoting peptide sequence to be introduced more efficiently into the cells.

Example 4: Evaluation of Calreticulin Expression-Promoting Activity of Synthetic Peptide in Stem Cells The calreticulin expression-promoting activity of the Samples 1 to 12 obtained in Example 1 was investigated. BXM14 cells, a cultured cell line of mouse ES cells (hereunder sometimes called "BXM14"), were used as the test cells. The details of the evaluation test were as follows.

The sample ES cells (BXM14) were seeded to a cell density of about $1 \times 10^4$ cells per well on 4-well slides. Using DMEM medium (Wako Pure Chemical, Cat No. 043-30085) containing 15% Knockout™ Serum Replacement (hereunder sometimes called "KSR"; Life Technologies, Cat No. 10828), 0.1 mM Non-essential Amino Acids Solution (hereunder sometimes called "NEAA"; Wako Pure Chemical, Cat No. 139-15651), 0.1 mM 2-mercaptoethanol (Sigma-Aldrich, Cat No. M7522) and 1000 units/mL of StemSure™ LIF, Mouse, recombinant, Solution (hereunder sometimes called "mLIF"; Wako Pure Chemical, Cat No. 199-116051), the cells were cultured overnight in an incubator under conditions of 5% $CO_2$, 37° C. The DMEM medium containing KSR, NEAA, 2-mercaptoethanol and mLIF is also called simply "ES DMEM medium". After the overnight culture, the medium was replaced with ES DMEM medium containing the peptides of Samples 1 to 12 in an amount yielding a peptide concentration of 50 μM, and the cells were cultured for 3 days. During this 3-day culture period, the medium was replaced every day with ES DMEM medium containing the peptides of Samples 1 to 12 in an amount yielding a peptide concentration of 50 μM. A peptide-free group was established as a control group.

After completion of this culture, calreticulin expression in each test group was investigated by the immunofluorescent antibody technique (fluorescent immunostaining) with an anti-calreticulin antibody as in Example 3 but using an anti-calreticulin monoclonal [FMC75] antibody (from mouse, Abcam, Cat. No. ab22683) diluted 400 times with 1% BSA/PBS (−) to a final concentration of $2.5 \times 10^{-3}$ mg/mL as the primary antibody, and an anti-mouse IgG antibody (goat, Life Technologies, A11029) labeled with a fluorescent dye (Alexa™ 488) and diluted 200 times with 1% BSA/PBS (−) to a final concentration of $10 \times 10^{-3}$ mg/mL as the secondary antibody.

Figure 16:
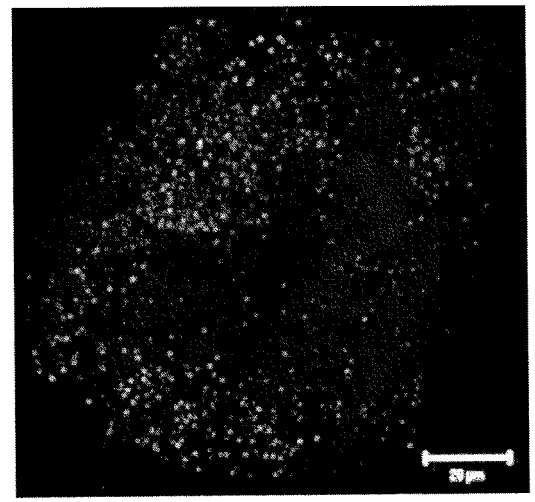
FIG. 16 is a fluorescence micrograph (image) examining the calreticulin expression state of ES (embryonic stem) cells cultured after addition of a calreticulin expression-promoting peptide (Sample 1) of one embodiment to those ES cells.
Figure 17:
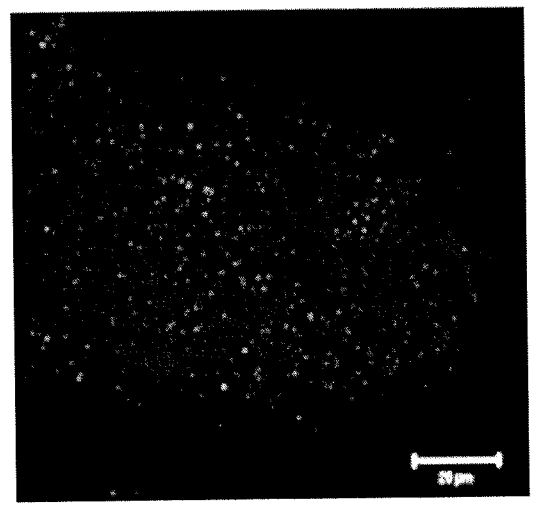
FIG. 17 is a fluorescence micrograph (image) examining the calreticulin expression state of ES cells cultured with no calreticulin expression-promoting peptide added to the ES cells.

The results of fluorescence observation by confocal laser microscopy are shown in FIG. 16 and FIG. 17. FIG. 16 shows the results for the Sample 1 group, while FIG. 17 shows the results for the peptide-free group. These figures (images) are fluorescence micrographs examining calreticulin expression in each test group, and each combines (merges) a fluorescent image showing results for calreticulin expression in ES cells as measured by the immunofluorescent antibody technique with an image showing nuclear staining by DAPI.

As shown in FIG. 16 and FIG. 17, with the ES cells (FIG. 16) treated with the synthetic peptide of Sample 1 (calreticulin expression-promoting peptide), the fluorescent label indicating calreticulin exhibited stronger fluorescence than in the case of the ES cells (FIG. 17) of the peptide-free group and the ES cells (not shown) treated with the synthetic peptide of Sample 12 (peptide comprising random amino acid sequence). Moreover, although these results are not shown in detail, in the case of the ES cells treated with the synthetic peptides of Samples 2 to 11 (calreticulin expression-promoting peptides), the fluorescent label indicating calreticulin also exhibited stronger fluorescence than in the case of the ES cells (FIG. 17) of the peptide-free group and the ES cells treated with the synthetic peptide of Sample 12. This confirms that the synthetic peptides of Samples 1 to 11 significantly increase the amount of calreticulin expression in ES cells.

Meanwhile, the synthetic peptides of Samples 9 to 11 having transmembrane peptide sequences were confirmed to increase the amount of calreticulin expression in ES cells as much as or more than the peptides of Samples 1, 3 and 5, which consisted solely of calreticulin expression-promoting peptide sequences.

These findings show that the calreticulin expression-promoting peptide disclosed here (that is, a calreticulin expression promoter containing this peptide as an active ingredient) is a peptide (composition) capable of dramatically increase the amount of calreticulin expression in stem cells (typically ES cells). They also show that a calreticulin expression-promoting peptide having a transmembrane peptide sequence exhibits stronger calreticulin expression promoting activity because the transmembrane peptide sequence causes the calreticulin expression-promoting peptide sequence to be introduced more efficiently into the cells.

Example 5: Preparation of Granules 50 mg of the synthetic peptides (calreticulin expression-promoting peptides) of Samples 1 to 11 above were mixed with 50 mg of crystalline cellulose and 400 mg of lactose, and kneaded after addition of 1 mL of a mixed solution of ethanol and water. The kneaded product was granulated by ordinary methods to obtain granules (granulated composition) having the calreticulin expression-promoting peptide disclosed here as an active ingredient.

INDUSTRIAL APPLICABILITY

As discussed above, with the present invention it is possible to promote calreticulin expression (or increase the expressed amount of calreticulin) in at least one kind of eukaryotic cell, such as a tumor cell, stem cell or neural cell, and especially in genomically unstable cells. Thus, the present invention can be used for removing genomically unstable cells (such as tumor cells) from the living body, or for in vitro cell sorting (for example, sorting of genomically stable cells and genomically unstable cells) or the like. The present invention can be applied favorably to medical industries and medical research for example.

REFERENCE SIGNS LIST (Sequence Listing Free Text)
SEQ ID NOs: 1 to 78 Synthetic peptides

---

The invention claimed is:

1. A composition for use in promoting expression of calreticulin in at least one kind of eukaryotic cell, comprising:
   a pharmaceutically acceptable carrier; and
   a synthetic peptide, comprising the amino acid sequence represented by any one of SEQ ID NOs: 6-9, 11, 15, 19, 23, 28, 34-36, 38, 40, and 63,
   wherein a total number of amino acid residues constituting the synthetic peptide is 30 or fewer.

2. The composition according to claim 1, wherein the eukaryotic cell is a tumor cell or stem cell from a human or non-human mammal.

3. The composition according to claim 1, wherein the synthetic peptide comprises the amino acid sequence represented by any one of SEQ ID NOs: 6, 8, 28 and 63.

4. A composition for use in promoting expression of calreticulin in at least one kind of eukaryotic cell, comprising:

a pharmaceutically acceptable carrier; and
a synthetic peptide, comprising the amino acid sequence represented by any one of SEQ ID NOs: 6-12, 14-17, 19, 21, 23, 27-30, 32, 34-42, 44, and 63, wherein
the synthetic peptide has a transmembrane peptide sequence at the N-end or C-end of the amino acid sequence represented by any one of SEQ ID NOs: 6-12, 14-17, 19, 21, 23, 27-30, 32, 34-42, 44, and 63, and
a total number of amino acid residues constituting the synthetic peptide is 30 or fewer.

5. The composition according to claim 4, wherein the eukaryotic cell is a tumor cell or stem cell from a human or non-human mammal.

6. The composition according to claim 4, wherein the transmembrane peptide sequence is

KKRTLRKNDRKKR. (SEQ ID NO: 1)

7. A synthetic peptide for use in promoting expression of calreticulin in at least one kind of eukaryotic cell, the peptide comprising
the amino acid sequence represented by any one of SEQ ID NOs: 8-12, 14-17, 19, 21, 23, 27-30, 32, 34-42, and 44, wherein
the synthetic peptide has a transmembrane peptide sequence at the N-end or C-end of the amino acid sequence represented by any one of SEQ ID NOs: 8-12, 14-17, 19, 21, 23, 27-30, 32, 34-42, and 44, and
a total number of amino acid residues constituting the synthetic peptide is 30 or fewer.

8. The synthetic peptide according to claim 7, wherein the eukaryotic cell is a tumor cell or stem cell from a human or non-human mammal.

9. The synthetic peptide according to claim 7, wherein the transmembrane peptide sequence is

KKRTLRKNDRKKR. (SEQ ID NO: 1)

10. A composition for use in promoting expression of calreticulin in at least one kind of eukaryotic cell, comprising:
a pharmaceutically acceptable carrier; and
a chemically synthetic peptide, consisting of the amino acid sequence represented by any one of SEQ ID NOs: 10, 12, 14, 16, 21, 25-27, 29, 30, 32, 33, 37, 39, 41, 42, and 44, wherein the C-terminal is amidated.

11. The composition according to claim 10, wherein the eukaryotic cell is a tumor cell or stem cell from a human or non-human mammal.

* * * * *